(12) United States Patent
Foilman et al.

(10) Patent No.: US 11,123,535 B2
(45) Date of Patent: Sep. 21, 2021

(54) METHOD AND ANTIMICROBIAL CAP FOR DISINFECTING A PORT

(71) Applicant: PROFESSIONAL DISPOSABLES INTERNATIONAL, INC., Orangeburg, NY (US)

(72) Inventors: Mark Foilman, Glen Rock, NJ (US); Jesse R. Dlugos, Woodbridge, CT (US); Kathryn Spencer, San Diego, CA (US); Jeffrey E. Ransden, Fairfield, CT (US); John Tanayan, Ridgefield Park, NJ (US)

(73) Assignee: PROFESSIONAL DISPOSABLES INTERNATIONAL, INC., Orangeburg, NY (US)

( * ) Notice: Subject to any disclaimer, the term of this patent is extended or adjusted under 35 U.S.C. 154(b) by 678 days.

(21) Appl. No.: 15/916,891

(22) Filed: Mar. 9, 2018

(65) Prior Publication Data
US 2018/0256880 A1 Sep. 13, 2018

Related U.S. Application Data

(60) Provisional application No. 62/469,273, filed on Mar. 9, 2017.

(51) Int. Cl.
*A61L 2/00* (2006.01)
*B08B 3/04* (2006.01)
(Continued)

(52) U.S. Cl.
CPC .............. *A61M 39/162* (2013.01); *A61L 2/18* (2013.01); *A61M 39/20* (2013.01);
(Continued)

(58) Field of Classification Search
CPC .... A61L 2/18; A61L 2101/00; A61L 2202/23; A61L 2202/24; A61L 2/0082; A61L 2/0088; A61L 2/16; A61L 2300/00; A61K 9/00; A61J 1/00; A61J 3/00; A61B 19/34; A61M 39/16; A61M 39/20
(Continued)

(56) References Cited

U.S. PATENT DOCUMENTS 7,282,186 B2    10/2007  Lake, Jr. et al.
D607,325 S       1/2010  Rogers et al.
(Continued)

FOREIGN PATENT DOCUMENTS

WO    WO 2016/044821 A1    3/2016

OTHER PUBLICATIONS

U.S. Appl. No. 15/917,128, filed Mar. 9, 2018.

*Primary Examiner* — Monzer R Chorbaji
(74) *Attorney, Agent, or Firm* — Baker Botts L.L.P.

(57) ABSTRACT

An antimicrobial cap and method for inhibiting the growth of microbes and disinfecting a port are disclosed. The antimicrobial cap comprises an assembly that includes an outer cap, an inner component and a pad disposed within the inner component and impregnated with an antimicrobial element in order to disinfect the port. The antimicrobial cap includes flexible attachment features configured to engage a port and a lockout mechanism configured to prevent and disable re-use of the cap, allowing the disinfection of different types of ports and connectors and safe disengagement of a single-use cap.

23 Claims, 20 Drawing Sheets

(51) Int. Cl.
*A61M 5/32* (2006.01)
*A61M 39/16* (2006.01)
*A61M 39/20* (2006.01)
*A61L 2/18* (2006.01)
*B65D 75/36* (2006.01)

(52) U.S. Cl.
CPC ..... *A61L 2202/121* (2013.01); *A61L 2202/15* (2013.01); *A61L 2202/24* (2013.01); *A61M 2205/0205* (2013.01); *A61M 2205/273* (2013.01); *A61M 2209/06* (2013.01); *B65D 75/367* (2013.01)

(58) Field of Classification Search
USPC ........... 422/544–546, 292, 300, 28; 604/192, 604/187; 134/104.1
See application file for complete search history.

(56) References Cited

U.S. PATENT DOCUMENTS

| | | | |
|---|---|---|---|
| 8,419,713 | B1 | 4/2013 | Solomon et al. |
| 8,740,864 | B2 * | 6/2014 | Hoang ................. A61M 39/02 604/267 |
| 8,999,073 | B2 * | 4/2015 | Rogers ...................... A61L 2/18 134/115 R |
| 9,283,369 | B2 | 3/2016 | Ma et al. |
| 9,352,140 | B2 | 5/2016 | Kerr et al. |
| 2007/0018014 | A1 * | 1/2007 | Finell ..................... A47K 3/005 239/288 |
| 2011/0217212 | A1 * | 9/2011 | Solomon ............. A61M 39/165 422/292 |
| 2012/0302997 | A1 | 11/2012 | Gardner et al. |
| 2014/0358115 | A1 | 12/2014 | Chelak et al. |
| 2015/0217106 | A1 | 8/2015 | Banik et al. |
| 2015/0314120 | A1 | 11/2015 | Gardner |
| 2016/0144118 | A1 | 5/2016 | Solomon et al. |
| 2017/0056640 | A1 | 3/2017 | Tennican |

* cited by examiner

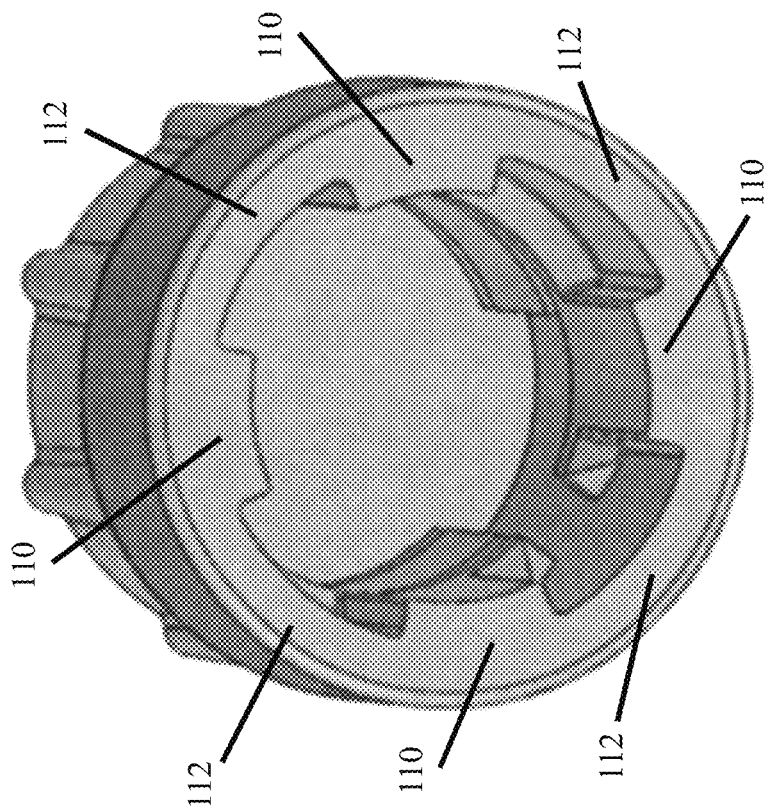
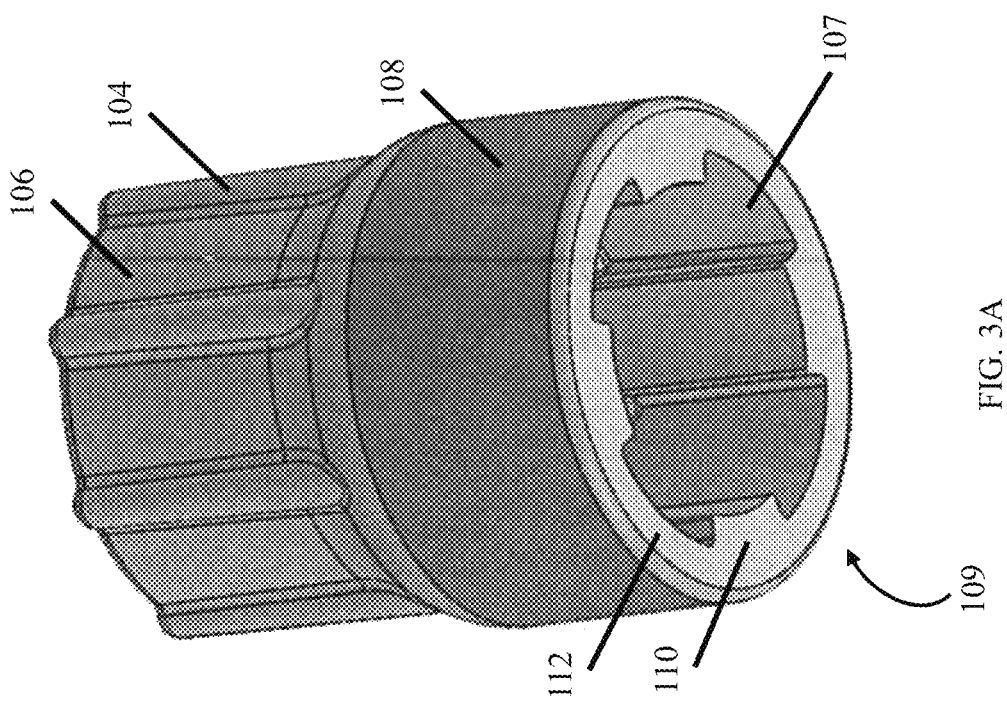
FIG. 3B
FIG. 3A

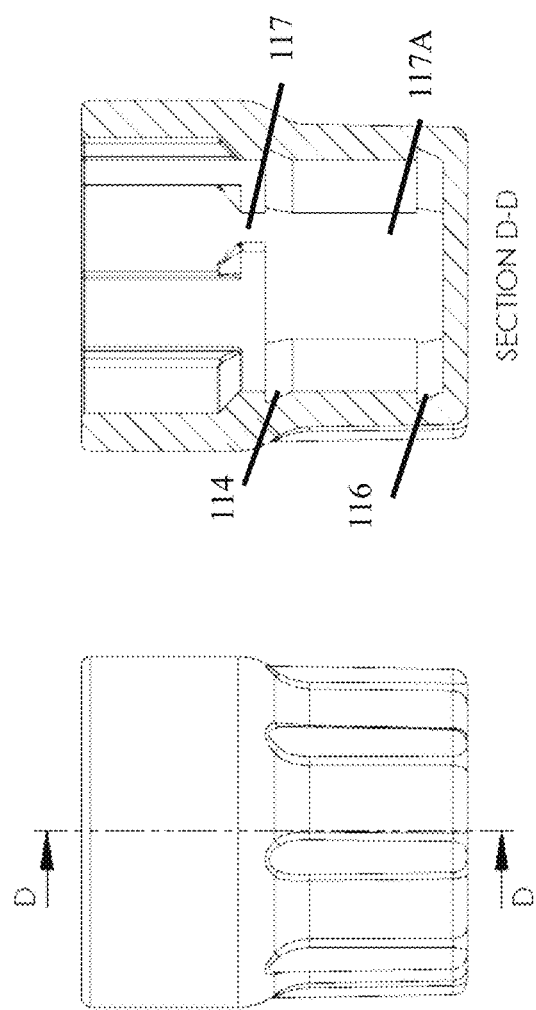
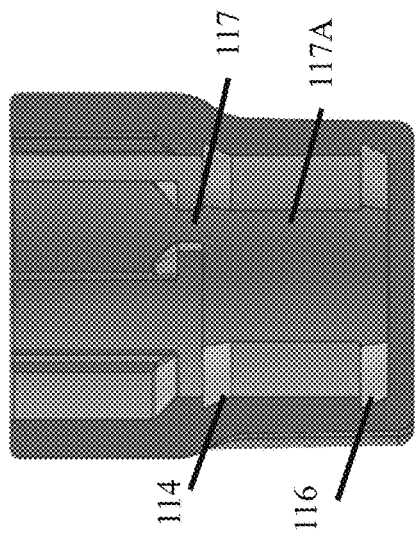
FIG. 4G
FIG. 4H
FIG. 4I

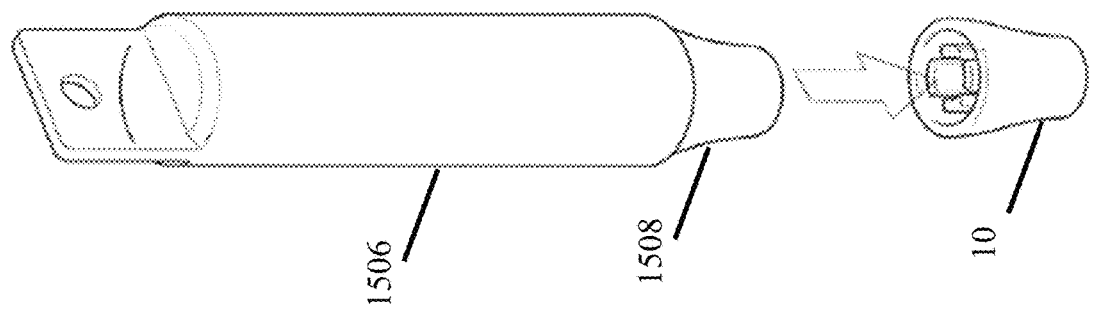
FIG. 15E
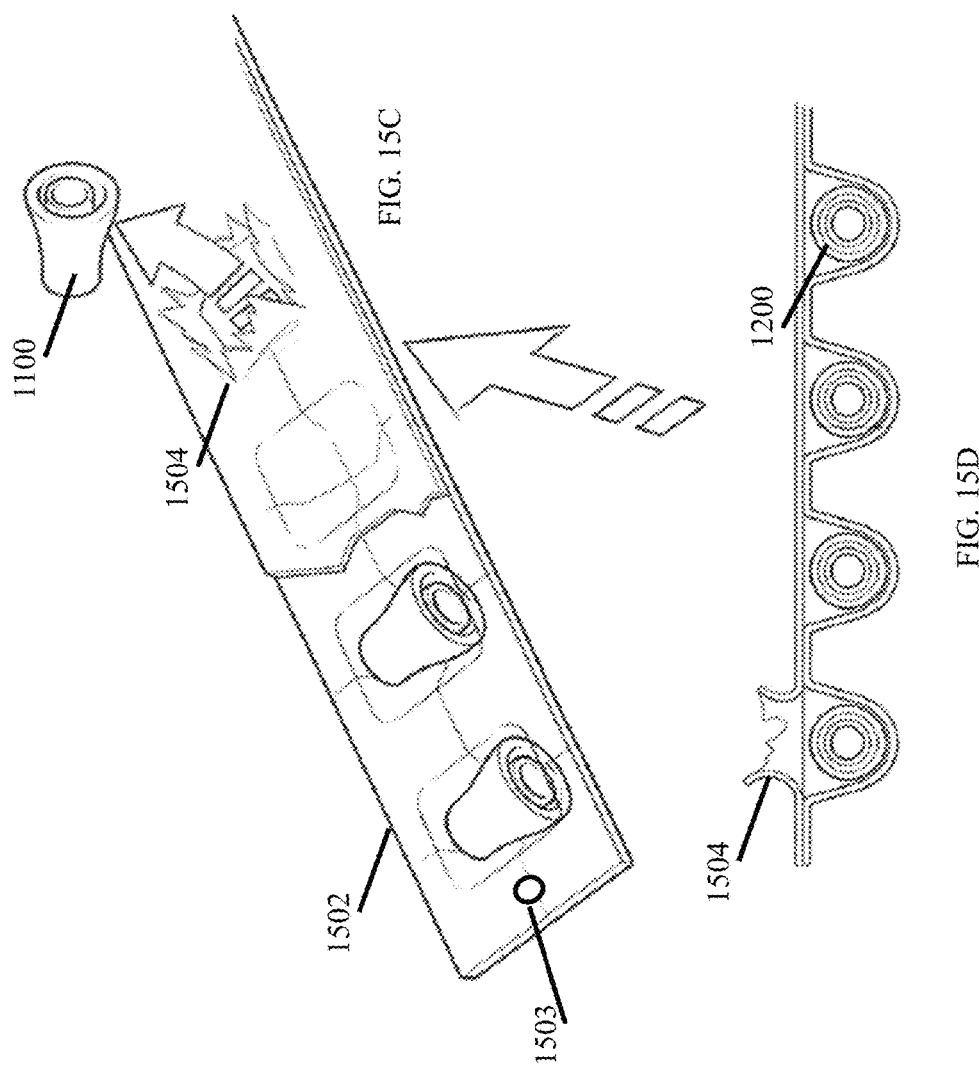
FIG. 15C
FIG. 15D

METHOD AND ANTIMICROBIAL CAP FOR DISINFECTING A PORT

CROSS-REFERENCE TO RELATED APPLICATIONS

This application claims priority to U.S. Provisional Application No. 62/469,273, filed on Mar. 9, 2017, the contents of which is hereby incorporated by reference in its entirety.

FIELD OF THE DISCLOSED SUBJECT MATTER

The disclosed subject matter relates to an antimicrobial cap. Specifically, the anti-microbial cap is attachable to a port to disinfect the port and the cap is thereafter disabled in order to prevent re-use of the antimicrobial cap.

BACKGROUND OF THE DISCLOSED SUBJECT MATTER

A variety of caps that are commonly used to treat ports and other medical connectors typically include an open end, a closed end and a cavity in which the port is received. Furthermore, the cavity can include a foam or non-woven material having a disinfecting solution therein for cleaning the port. Examples of medical connectors for which such caps are used are intravascular connectors associated with a fluid pathway, such as a central line, connectors associated with an intravenous bag, luer lock connectors, connectors associated to medical catheters and others. These connectors require careful handling and disinfection prior to use on a port connected to a patient since the use of various fluid reservoirs can increase the risk of infections due to possible contamination factors relating to frequent use and fluid transfer. However, in many cases the provided caps need to be manufactured for specific connectors and must include additional structures such as threads to be able to securely engage the medical connectors and/or ports. Further, such caps lack the functionality or ability to prevent a user from reusing the cap a subsequent time. Therefore, it would be an advantage to have a cap that can be used to provide protection for different types of medical connectors/ports, and have the ability to prevent re-use.

There thus remains a continued need for an efficient and safe antimicrobial cap for cleaning and disinfecting a port that includes a disabling feature to ensure that the antimicrobial cap is non-reusable. The presently disclosed subject matter satisfies these and other needs.

SUMMARY OF THE DISCLOSED SUBJECT MATTER

The purpose and advantages of the disclosed subject matter will be set forth in and are apparent from the description that follows, as well as will be learned by practice of the disclosed subject matter. Additional advantages of the disclosed subject matter will be realized and attained by the devices particularly pointed out in the written description and claims hereof, as well as from the appended drawings.

To achieve these and other advantages and in accordance with the purpose of the disclosed subject matter, as embodied and broadly described, the disclosed subject matter includes an antimicrobial cap to treat a port, the antimicrobial cap comprising an outer cap having an open end, a closed end and defining a cavity therein, the outer cap having a sidewall with an inner surface that defines an engagement structure. An inner component receivable in the outer cap, the inner component having a distal end comprising a first attachment member that engages with the engagement structure of the outer cap and a proximal end comprising a second attachment member to engage the port, wherein the proximal end of the inner component is aligned with a proximal end of the outer cap in a first position, and the second attachment member is at least partially disposed within the cavity of the outer cap in a second position, the inner component being axially movable from the first position to the second position with respect to the outer cap, and the outer cap being rotatable with respect to the inner component, and a pad disposed within a chamber of the inner component, the pad impregnated with an antimicrobial element, wherein the port is receivable in the chamber as the second attachment member engages an external surface of the port, the pad being compressed by the port to release the antimicrobial element therefrom when the inner component moves from the first position towards the second position to engage the inner component to the port, wherein the outer cap is rotatable about the inner component to a third position to disengage the inner component from the port such that the inner component remains coupled within the cavity of the outer cap upon disengagement.

In accordance with another aspect of the disclosed subject matter, a method of inhibiting the growth and disinfecting a port is provided. Specifically, the disclosed subject matter comprises providing an outer cap having an open end, a closed end and defining a cavity therein, the outer cap having a sidewall with an inner surface that defines an engagement structure, an inner component receivable in the outer cap, the inner component having a distal end comprising a first attachment member that engages with the engagement structure of the outer cap and a proximal end comprising a second attachment member to engage the port, wherein the proximal end of the inner component is aligned with a proximal end of the outer cap in a first position, and the second attachment member is at least partially disposed within the cavity of the outer cap in a second position, the inner component being axially movable from the first position to the second position with respect to the outer cap, and the outer cap being rotatable with respect to the inner component, a pad disposed within a chamber of the inner component, the pad impregnated with an antimicrobial element; receiving the port in the chamber as the second attachment member engages an external surface of the port; moving the inner component from the first position towards the second position to engage the inner component to the port; compressing the pad with the port to release the antimicrobial element therefrom; and rotating the outer cap about the inner component to a third position to disengage the inner component from the port such that the inner component remains coupled within the cavity of the outer cap upon disengagement.

In accordance with another aspect of the disclosed subject matter, an antimicrobial cap to treat a port is provided, the antimicrobial cap comprising: an outer cap having an open end, a closed end and defining a cavity therein, the outer cap having a sidewall with an inner surface that defines an engagement structure; an inner component receivable in the outer cap, the inner component having a distal end comprising an attachment member that engages with the engagement structure of the outer cap and a proximal end comprising a flexible chamber to engage the port, wherein the proximal end of the inner component is aligned with a proximal end of the outer cap in a first position, and the flexible chamber is at least partially disposed within the cavity of the outer cap in a second position, the inner component being axially movable from the first position to the second position with respect to the outer cap, and the outer cap being rotatable with respect to the inner component; and a pad disposed within a chamber of the inner component, the pad impregnated with an antimicrobial element, wherein the port is receivable in the chamber as the flexible chamber engages an external surface of the port, the pad being compressed by the port to release the antimicrobial element therefrom when the inner component moves from the first position towards the second position to engage the inner component to the port, wherein the outer cap is rotatable about the inner component to a third position to disengage the inner component from the port such that the inner component remains coupled within the cavity of the outer cap upon disengagement.

In accordance with another subject of the disclosed subject matter, an antimicrobial cap to treat a port, the antimicrobial cap comprising an outer cap having an open end, a closed end and defining a cavity therein, the outer cap having a sidewall with an inner surface that defines an engagement structure. An inner component receivable in the outer cap, the inner component having a distal end comprising a first attachment member that engages with the engagement structure of the outer cap and a proximal end comprising a second attachment member to engage the port, wherein the second attachment member of the inner component is at least partially disposed outside the cavity of the outer cap in a first position, and the second attachment member is at least partially disposed within the cavity of the outer cap in a second position, the inner component being axially movable from the first position to the second position with respect to the outer cap, and the outer cap being rotatable with respect to the inner component, and a pad disposed within a chamber of the inner component, the pad impregnated with an antimicrobial element, wherein the port is receivable in the chamber as the second attachment member engages an external surface of the port, the pad being compressed by the port to release the antimicrobial element therefrom when the inner component moves from the first position towards the second position to engage the inner component to the port, wherein the outer cap is rotatable about the inner component to a third position to disengage the inner component from the port such that the inner component remains coupled within the cavity of the outer cap upon disengagement.

It is to be understood that both the foregoing general description and the following detailed description and drawings are examples and are provided for purpose of illustration and not intended to limit the scope of the disclosed subject matter in any manner.

The accompanying drawings, which are incorporated in and constitute part of this specification, are included to illustrate and provide a further understanding of the devices of the disclosed subject matter. Together with the description, the drawings serve to explain the principles of the disclosed subject matter.

BRIEF DESCRIPTION OF THE DRAWINGS

The subject matter of the application will be more readily understood from the following detailed description when read in conjunction with the accompanying drawings, in which:

FIG. 3A is a perspective view of a first end of the outer cap of FIG. 2, in accordance with the disclosed subject matter.

FIG. 3B is a bottom perspective plan view of the outer cap of FIG. 2, in accordance with the disclosed subject matter.

FIG. 4G is a side view of the outer cap of FIG. 2, in accordance with an embodiment the disclosed subject matter.

FIG. 4H is a side cross-sectional perspective view through section D-D of the outer cap of FIG. 4G, in accordance with the disclosed subject matter.

FIG. 4I is a side cross-sectional perspective view of the outer cap of FIG. 4G, in accordance with the disclosed subject matter.

FIG. 15C is a top perspective view of a blister packaging for a plurality of antimicrobial caps, in accordance with an alternate embodiment.

FIG. 15D is a side cross-sectional view of a portion of the blister packaging of FIG. 15C in accordance with the disclosed subject matter.

FIG. 15E is a side perspective view of a packaging dispenser for a plurality of antimicrobial caps, in accordance with an alternate embodiment.

DETAILED DESCRIPTION

Figure 1:
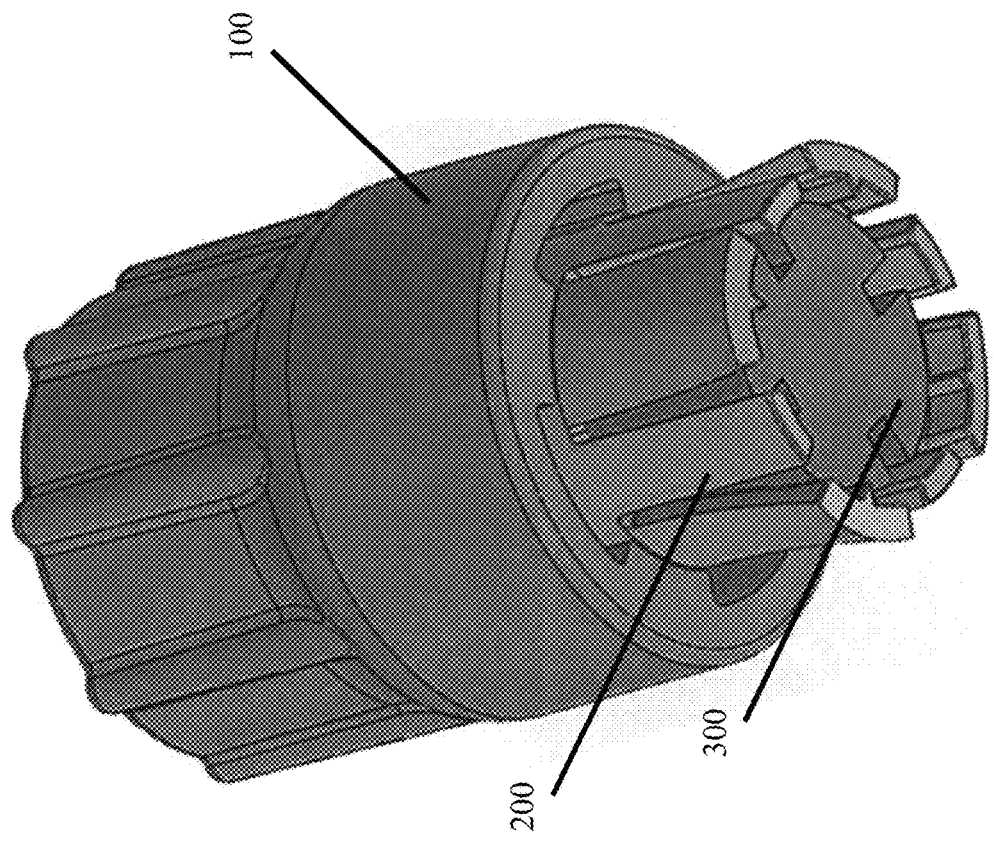
FIG. 1 is a bottom perspective view of an antimicrobial cap in a first position in accordance with an embodiment of the disclosed subject matter.

Reference will now be made in detail to embodiments of the disclosed subject matter, an example of which is illustrated in the accompanying drawings. The disclosed subject matter will be described in conjunction with the detailed description of the system.

The terms used in this specification generally have their ordinary meanings in the art, within the context of this subject matter and in the specific context where each term is used. Certain terms are defined below to provide additional guidance in describing the compositions and methods of the disclosed subject matter and how to make and use them.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to systems or processes, the term can mean within an order of magnitude, preferably within 5-fold, and more preferably within 2-fold, of a value.

As disclosed herein, the antimicrobial cap presented herein can be used to inhibit the growth of microbes and/or to disinfect a port. The antimicrobial cap includes an outer cap, inner component and a pad that contains an antimicrobial agent e.g., a solution that disinfects a medical port upon contact. The aforementioned port can include access ports on tubing sets (i.e., such as extension sets, Y-connectors and IV sets), access ports on catheters, valves, luer connectors, stethoscopes and other connecting components or any suitable device where disinfection is desired.

In accordance with the disclosed subject matter, an antimicrobial cap having an outer cap, an inner component and a pad that is impregnated with an antimicrobial element such as, for example, a disinfecting solution is provided. The pad can be disposed within a chamber of the inner component and, in turn, having the inner component at least partially disposed within the outer cap such that the port is receivable in the chamber of the inner component and is contacted with the pad. Specifically, the outer cap has a closed end and an open end that defines a cavity. Furthermore, the cavity has a sidewall with an inner surface that includes an engagement structure in order to engage the inner component of the antimicrobial cap. The inner component, which is receivable in the outer cap, has a distal end that includes one or more legs that engage and attach with the outer cap and has a proximal end that can include one or more arms that engage and attach to the port. Once the port connects to the antimicrobial cap, the port can be axially pushed to a position whereby the port compresses the pad and releases the antimicrobial element therefrom. As a result of the movement, the arms of the inner component are partially disposed within the cavity of the outer cap. Furthermore, once the port is engaged to the antimicrobial cap at this position, the inner component becomes rotatable with respect to the outer cap. Such movement allows for the legs of the inner component to lock with the outer cap causing disengagement of the port from the antimicrobial cap while the inner component remains coupled within the cavity of the outer cap upon the disengagement of the port.

Solely for purpose of illustration, an exemplary embodiment of an antimicrobial cap, is shown schematically in FIG. 1. The examples herein are not intended to limit the scope of the disclosed subject matter in any manner. Particularly, and as illustrated, the antimicrobial cap 10 includes an outer cap 100, inner component 200 and pad 300. Specifically, when the antimicrobial cap 100 is in a use position, a portion of inner component 200 is located outside the outer cap 100 in order to engage a port of a medical device.

Figure 2:
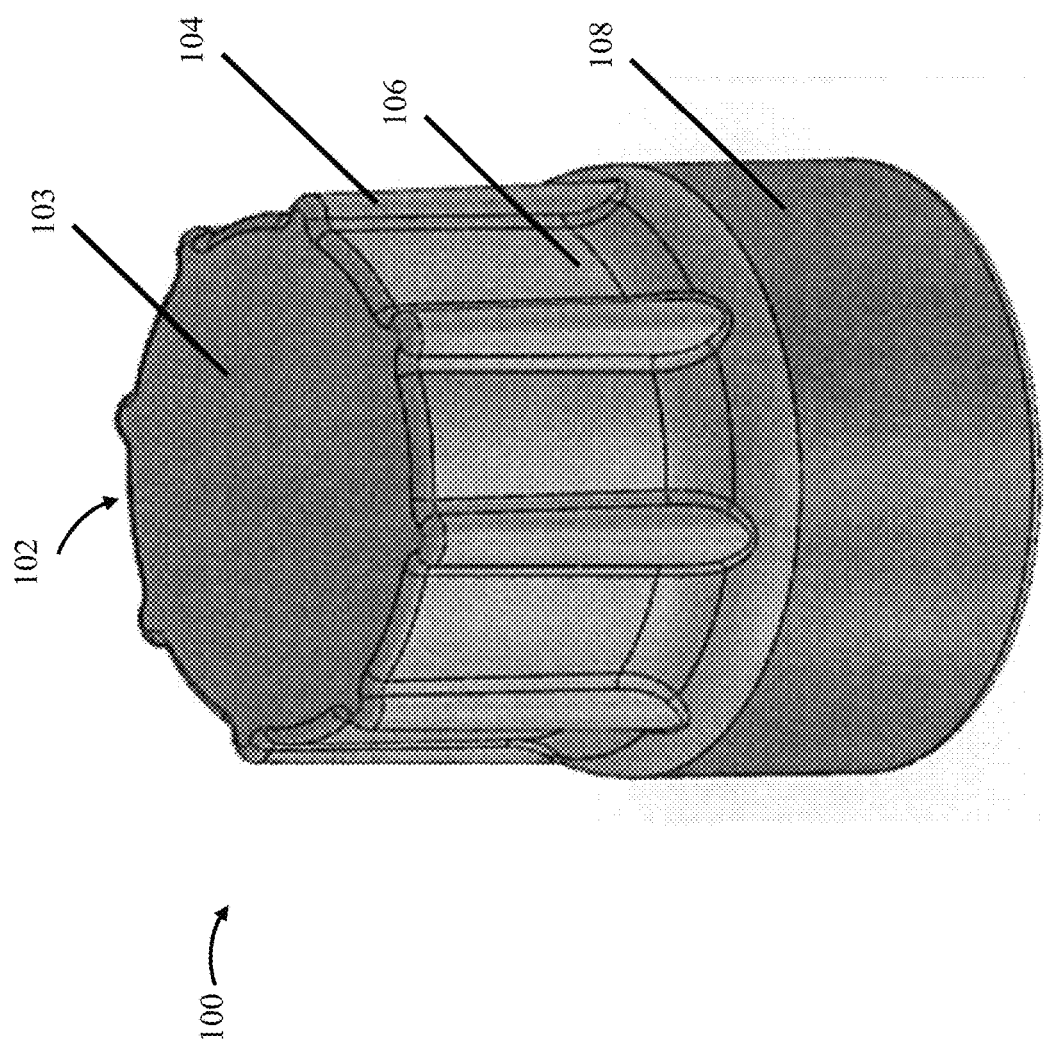
FIG. 2 is a top perspective view of the outer cap of FIG. 1, in accordance with the disclosed subject matter.

FIG. 2 shows a top perspective view of outer cap 100 that includes a closed end 102, an open end (not shown in this view), a skirt 108 and a sidewall that defines an external engagement structure that includes alternating projections 104 and depressed surfaces 106. Closed end 102 can include a top surface 103 as shown. The sidewall is connected to the top surface 103 along a perimeter thereof. The sidewall can include one or more projections 104 on an exterior thereof configured to engage a housing, as discussed further herein. The sidewall can also include a skirt 108 at a bottom portion thereof. In some embodiments, the skirt 108 can have a larger diameter than the sidewall of outer cap 100 to allow for different types of medical devices to become attached and treated. In some embodiments, alternating projections 104 and depressed surfaces 106 can extend along the external surface of skirt 108 or in any other suitable combination. In some embodiments, the outer cap 100 can be of plastic, polymer and/or any other suitable material and can be manufactured using various techniques such as casting, molding, 3D printing and/or any other suitable process.

Solely for purpose of illustration, reference is now made to FIGS. 3A-3B showing a perspective view of a first end and a bottom perspective plan view of outer cap 100 respectively. Specifically, outer cap 100 has a closed end 102 and an open end 109 that define a cavity in which inner component 200 can be disposed. Moreover, the outer cap 100 has a sidewall that further defines an inner surface 107. The inner surface has an engagement structure that includes alternating longitudinal channels 112 and abutment surfaces 110 that allow for receiving inner component 200. In some embodiments, alternating longitudinal channels 112 and abutment surfaces 110 are located along the inner surface of skirt 108. In some embodiments, alternating longitudinal channels 112 and abutment surfaces 110 extend along the entirety of the inner surface 107 of outer cap 100 from closed end 102 and to the open end 109. In some embodiments, longitudinal channels 112 are wider than abutment surfaces 110 to allow for different types of medical devices to become attached to inner component 200 and be disinfected.

Figure 4C:
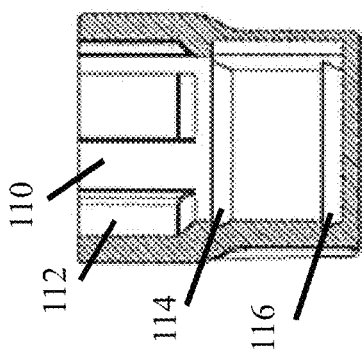
FIG. 4C is a side cross-sectional perspective view of the outer cap of FIG. 4B, in accordance with the disclosed subject matter.
Figure 4F:
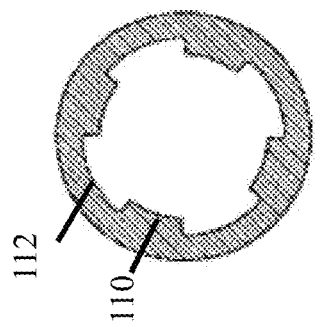
FIG. 4F is a top cross-sectional perspective view through Section B-B of the outer cap of FIG. 4B, in accordance with the disclosed subject matter.
Figure 4B:
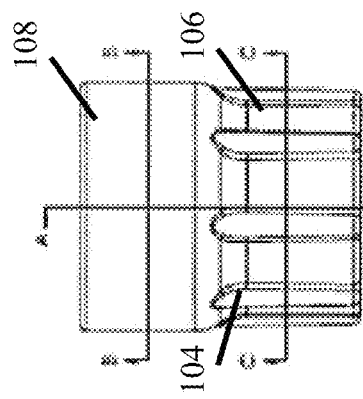
FIG. 4B is a side view of the outer cap of FIG. 2, in accordance with the disclosed subject matter.
Figure 4E:
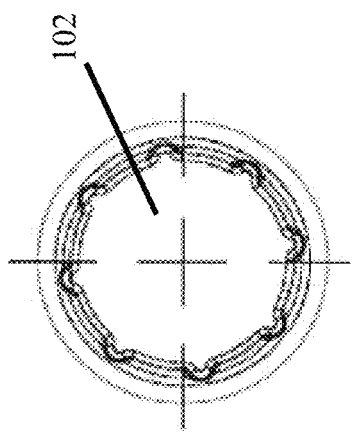
FIG. 4E is a top plan view of the outer cap of FIG. 2, in accordance with the disclosed subject matter.
Figure 4A:
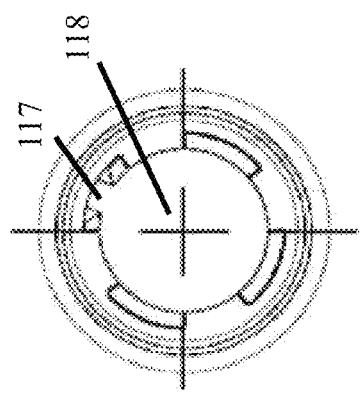
FIG. 4A is a bottom view of the outer cap of FIG. 2, in accordance with the disclosed subject matter.

FIGS. 4A-4F show various views and cross-sections of outer cap 100 in accordance with some embodiments of the disclosed subject matter. FIG. 4A shows a bottom view of outer cap 100 including cavity 118 and alignment key surface 117 that receives inner component 200. In some embodiments, alignment key surface 117 aligns inner component 200 with the outer cap 100 during assembly and use of the antimicrobial cap 10. FIG. 4B is a side view of outer cap 100 including cross-sectional lines A-A, B-B and C-C that are represented in FIGS. 4C-4F, respectively. Specifically, FIG. 4C shows a side cross-sectional perspective view of outer cap 100 along cross-sectional lines A-A, as referenced in connection to FIG. 4B. As shown, the outer cap 100 includes longitudinal channels 112 and abutment surfaces 110 extending along the inner surface of the sidewall of skirt 108. In addition, in some embodiments, inner surface 107 of outer cap 100 can also include sets of female depressions/grooves 114 and 116, as further discussed herein.

Figure 4D:
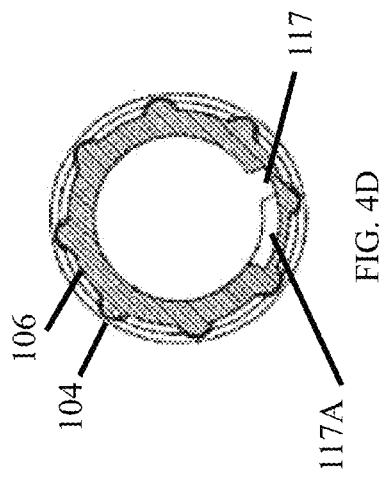
FIG. 4D is a top cross-sectional perspective view through Section C-C of the outer cap of FIG. 4B, in accordance with the disclosed subject matter.

FIG. 4D shows a top cross-sectional perspective view of outer cap 100 along lines C-C illustrated in FIG. 4B. Specifically, alternating projections 104 and depressed surfaces 106 are illustrated such that they extend radially along the external surface of the sidewall of outer cap 100. In some embodiments, longitudinal channels 112 and abutment surfaces 110 extend along a portion of inner surface 107, whereas the remaining portion of the inner surface 107 includes an even surface. In some embodiments, the inner surface of the sidewall proximate to closed end 102 includes one or more engagement structures, such as sets of female depressions/grooves 114 and 116, in order to receive the inner component 200. In some embodiments, the sets of female depressions/grooves 114 and 116 are located on opposite ends e.g., distanced from each other such that outer cap 100 can engage and lock inner component 200 during use for disinfecting a port. In some embodiments, locking inner component 200 to outer cap 100 during assembly and use of the antimicrobial cap 10 is accomplished by including alignment key surface 117 in the inner surface of the sidewall of outer cap 100. Furthermore, FIG. 4E shows a top view of outer cap 100 including closed end 102 and FIG. 4F shows a top cross-sectional perspective view of outer cap 100 along cross-sectional lines B-B as referenced in connection to FIG. 4B. As previously discussed, the inner surface of the sidewall of outer cap 100 includes the alternating longitudinal channels 112 and abutment surfaces 110, which is shown in the cross-sectional view of FIG. 4F. The widths and number of channels 112 and abutment surfaces 110 can be of any suitable value depending on inner component 200 and the type of port to be disinfected.

FIGS. 4G-4I show various views and cross-sections of outer cap 100 in accordance with some embodiments of the disclosed subject matter. FIG. 4G is a side view of outer cap 100 including cross-sectional line D-D that is represented in FIG. 4H. Specifically, FIG. 4H is a side cross-sectional perspective view through section D-D of the outer cap of FIG. 4G. As discussed above, FIG. 4H shows an engagement structure including two sets of female depressions/grooves 114 and 116 formed on the inner surface of the sidewall proximate to closed end 102 of outer cap 100. In some embodiments, such an engagement structure is configured to receive and ensure secure placement of the inner component 200 with respect to the outer cap 100. Furthermore, in some embodiments, the inner surface of the sidewall of outer cap 100 includes alignment key surface 117 such as a depression. For example, in some embodiments, such alignment key surface 117 can cooperate with an alignment key 203/209, which will be discussed below in connection with FIGS. 5A-5B, to provide alignment between the outer cap 100 and the inner component 200 during manufacturing and also provide a locking mechanism for safe use of the antimicrobial cap 10 and to facilitate proper rotational movement of the inner component with respect to the outer cap. In some embodiments, the use of an alignment key surface 117 and an alignment key 203/209 can restrict the degree of rotation and/or restrict the directionality of the rotation of the outer cap 100 during use and/or disengagement of the antimicrobial cap 10. For example, in some embodiments, disengaging the antimicrobial cap 10 once the alignment key surface 117 has been engaged by the alignment key 203/209, would be achieved through a counter-clockwise rotation of the outer cap with respect to the inner component. FIG. 4I shows a side cross-sectional perspective view of the outer cap of FIG. 4G including female depressions/grooves 114 and 116 and alignment key surface 117. The alignment key surface 117 can further define a longitudinal wall 117A, which restricts the direction the alignment key 203/209 can rotate. As such, the alignment key 203/209 is solely permitted to rotate away from the longitudinal wall 117A in the embodiment of FIG. 4I.

Figure 5B:
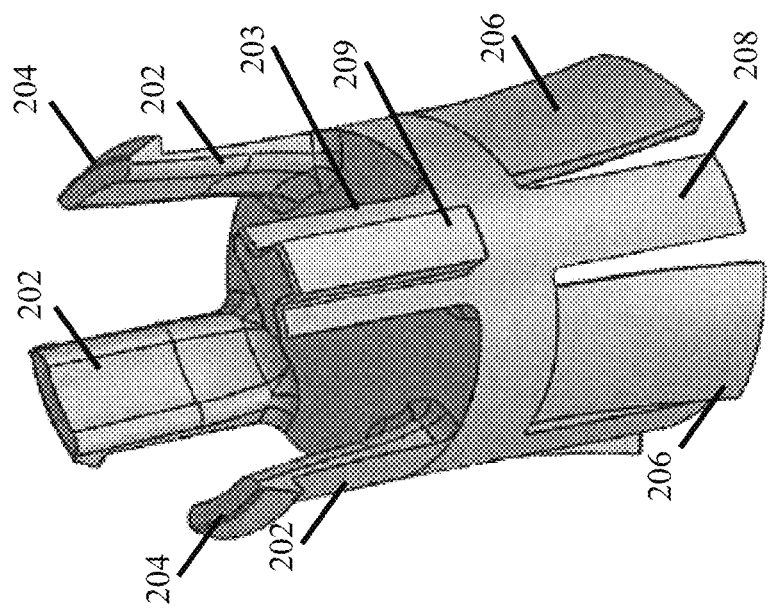
FIG. 5B is a top perspective view of the inner component of FIG. 5A, in accordance with the disclosed subject matter.
Figure 5A:
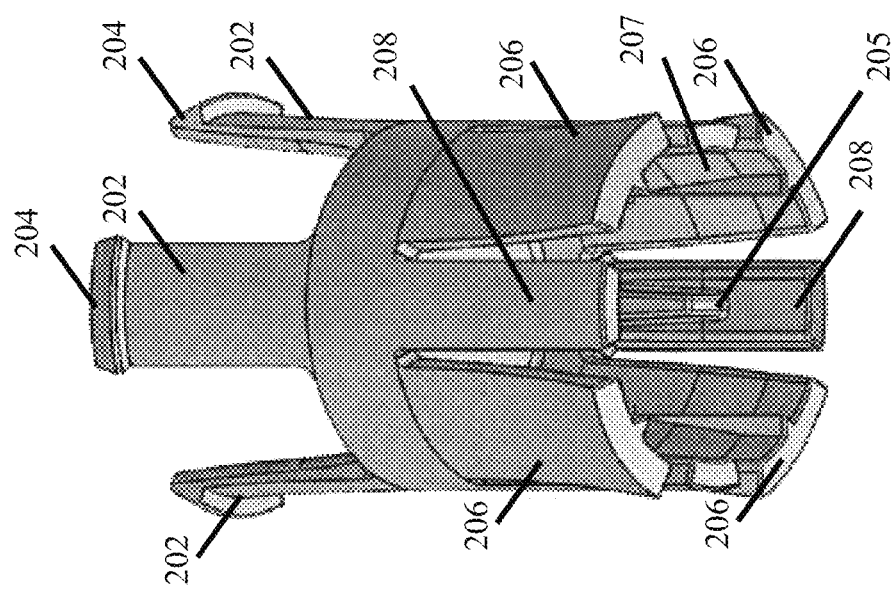
FIG. 5A is a bottom perspective view of the inner component of FIG. 1, in accordance with the disclosed subject matter.

Solely for purpose of illustration, reference is now made to FIGS. 5A-5B showing a bottom perspective view and top perspective view of inner component 200 respectively. Specifically, inner component 200 has a proximal end that engages and attaches to the port and a distal end that engages outer cap 100.

As illustrated in FIGS. 5A-5B, the proximal end of the inner component 200 provides an attachment structure that includes a plurality of attachment members. The attachment members can include both flexible arms 206 and rigid arms 208. The flexible arms and rigid arms can alternate, as shown. The flexible arms are outwardly biased which facilitates locking of the cap as further discussed herein. The rigid arms have less degree of flexibility as the flexible arms and extend uniformly. In some embodiments, the outwardly biased arms 206 have a greater width dimension than rigid arms 208, which can facilitate a stable and flexible coupling for different types and/or sizes of medical ports. In some embodiments, the number of arms 206 and 208 can vary based on the type of port that needs to be disinfected. For example, the inner component 200 can include four outwardly biased flexible arms 206 and four straight arms 208. In some embodiments, the outwardly biased arms 206 can include crush rib features (e.g., detent) 207 extending along each of the biased arms 206. In some embodiments, straight arms 208 can include axial alignment rib features (e.g., ridge) 205 extending along one or more of the straight arms 208. In some embodiments, axial alignment rib features 205 and crush rib features 207 can extend partially along straight arms 208 and outwardly biased arms 206 or in any other suitable manner.

In addition, in some embodiments, the attachment structure defines a chamber disposed within the alternating flexible arms that allows for the placement of a pad impregnated with one or more antimicrobial agents therein. Pad 300 contains any suitable antimicrobial element such as a disinfecting solution that disinfects the port upon contact. For example, in some embodiments, the antimicrobial element includes a solution such as alcohol, chlorhexidine gluconate and/or mixtures such as chlorhexidine-silver or any suitable combination thereof. In some embodiments, the pad includes grooves, slots and/or cut-outs that align to the alternating flexible arms of the proximal end of inner component 200 in order to secure the placement of the pad, such as grooves that complement the axial alignment rib features 205 and crush rib features 207. Furthermore, in some embodiments, the proximal end of inner component 200 provides a flexible chamber in which the pad is disposed and that allows for the coupling of the port to inner component 200. Specifically, such flexible chamber can include an inner surface including an engagement structure such as threads, or any other suitable connecting structure, that receives the port. In another embodiment, a portion of the proximal end of inner component 200 can include a flexible monolithic chamber and the remaining portion of the proximal end can include alternating flexible arms 206 and 208. As such, the proximal end of the inner component can be a combination of a flexible chamber and flexural arms and/or the arms can be partially joined. The attachment structure of inner component 200 can be made from any suitable material. For example, the alternating flexible arms can be made out of plastic, polymer (e.g., MDPE), silicone or any other suitable material that can be molded, cast and/or 3D printed. The manufacturing process used can be chosen to yield a part with built in stresses that bias the flexure of the arms.

As further illustrated, the distal end of inner component 200 also provides an attachment structure that includes a plurality of flexural attachment members. Specifically, these attachment members include flexible legs 202 that couple to the engagement structure disposed in the inner surface of outer cap 100. This allows for inner component 200 to firmly and permanently attach to outer cap 100. Accordingly, one or more of flexible legs 202 can include a protrusion 204 at the top of the leg that becomes engaged to female depressions/grooves 114 and 116 of outer cap 100 during use of the antimicrobial cap.

In some embodiments, inner component 200 includes four flexible legs 202 or any other suitable number that allows inner component 200 to firmly engage outer cap 100. In some embodiments, flexible legs 202 can be uniform, have the same dimensions and be disposed symmetrically about the diameter of the inner component. In some embodiments, flexible legs 202 can have any suitable size and placement in order to facilitate engagement to outer cap 100. The attachment structure of inner component 200 can be made with any suitable material. For example, the flexible legs can be made out of plastic, polymer (e.g., MDPE), silicone or any other suitable material that can be molded, cast and/or layer manufactured, such as 3D printed. The manufacturing process used can be chosen to yield a part with built in stresses that bias the flexure of the legs.

In other embodiments, inner component 200 further includes an alignment leg 203 with an alignment ridge 209 extending along the surface of alignment leg 203 in order to form an alignment key. In some embodiments, the alignment key (e.g., alignment leg 203 and alignment ridge 209) engages the alignment key surface 117 and the longitudinal wall 117A, as discussed in reference to FIGS. 4A and 4D, in order to lock the inner component 200 with the outer cap 100 during use of the antimicrobial cap. For example, in some embodiments, once the alignment key has engaged the alignment key surface 117, then the outer cap can move with respect to the inner component firstly in an axial direction to facilitate engagement with a port then secondly in a counterclockwise rotation that ensures disengagement of the antimicrobial cap from a port and locks the inner component 200 within the outer cap 100 to ensure that the antimicrobial cap cannot be re-used or re-engaged with a port. As such, the antimicrobial cap can be configured for single-use.

Figure 6D:
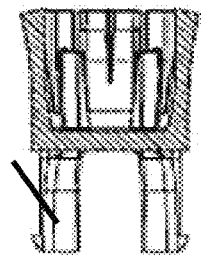
FIG. 6D is a side cross-sectional perspective view through Section A-A of a bottom portion of the inner component of the antimicrobial cap of FIG. 6B, in accordance with the disclosed subject matter.
Figure 6F:
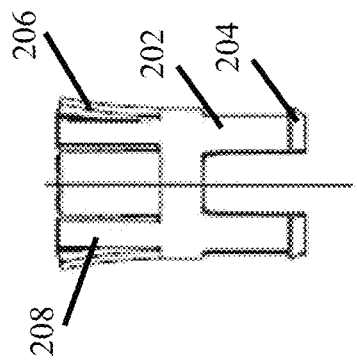
FIG. 6F is a side view of the inner component of the antimicrobial cap of FIG. 1, in accordance with the disclosed subject matter.
Figure 6B:
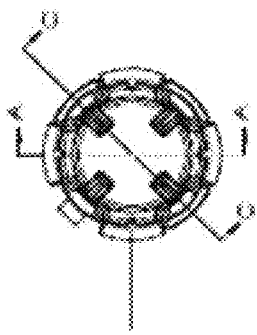
FIG. 6B is a bottom view of the inner component of the antimicrobial cap of FIG. 1, in accordance with the disclosed subject matter.
Figure 6A:
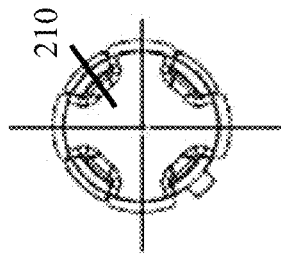
FIG. 6A is a top view of the inner component of the antimicrobial cap of FIG. 1, in accordance with the disclosed subject matter.
Figure 6C:
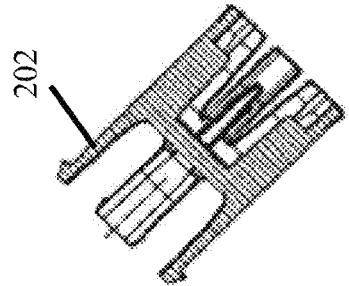
FIG. 6C is a side cross-sectional perspective view through Section C-C of the inner component of the antimicrobial cap of FIG. 6B, in accordance with the disclosed subject matter.
Figure 6E:
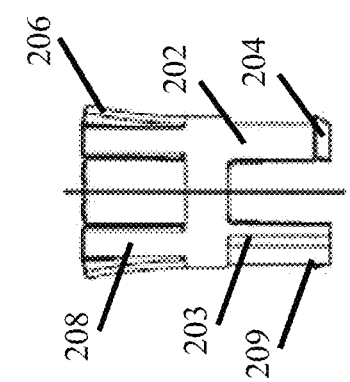
FIG. 6E is a side view of the inner component of the antimicrobial cap of FIG. 1, in accordance with the disclosed subject matter.

FIGS. 6A-6F show various views and cross-sections of inner component 200 in accordance with some embodiments of the disclosed subject matter. FIG. 6A shows a top view of the proximal end of inner component 200 including the chamber 210 that receives the pad 300. FIG. 6B is a bottom view of the distal end of inner component 200 including cross-sectional lines C-C and A-A that are represented in FIGS. 6C and 6D, respectively. Specifically, FIG. 6C shows a side cross-sectional perspective view of the distal end of inner component 200 along cross-sectional lines C-C as referenced in connection to FIG. 6B. As shown, inner component 200 includes flexible legs 202 that couple to the engagement structure disposed in the inner surface of outer cap 100 and allow for inner component 200 to firmly and permanently attach to outer cap 100. FIG. 6D shows a side cross-sectional perspective view of the proximal end of inner component 200 along cross-sectional lines A-A as referenced in connection to FIG. 6B. As shown, inner component 200 includes flexible arms 206 that define a chamber where the pad 300 is disposed and couple to the port. In addition, FIGS. 6E-6F show side views of inner component 200 including outwardly biased flexible arms 206, straight arms 208, legs 202, the alignment key with an alignment leg 203 and alignment ridge 209, and protrusion 204.

Figure 7:
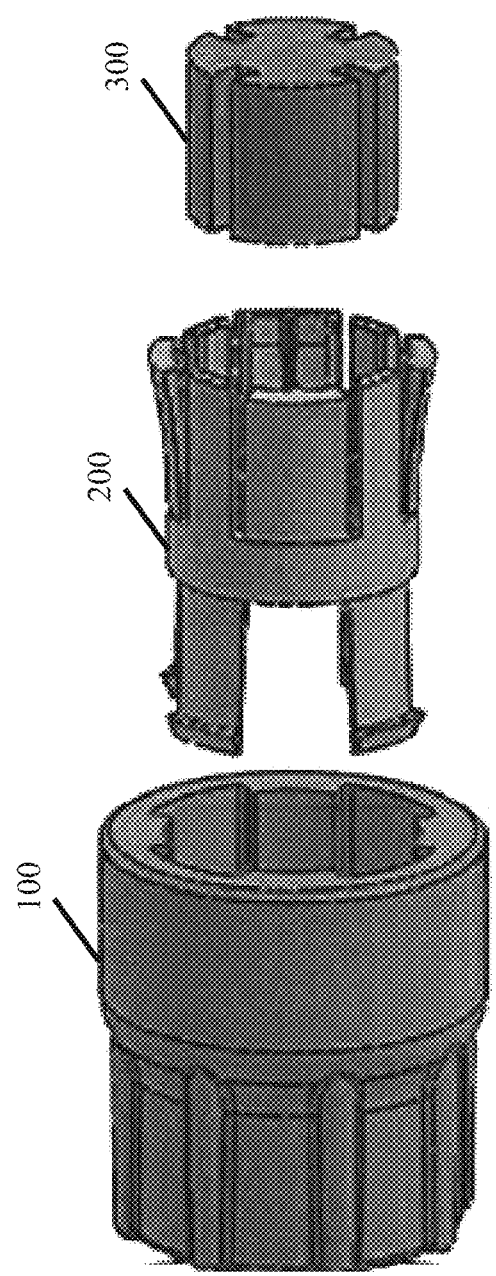
FIG. 7 is an exploded view of the antimicrobial cap of FIG. 1, in accordance with the disclosed subject matter.

FIG. 7 shows an exploded view of the antimicrobial cap in accordance with some embodiments of the disclosed subject matter. As discussed above in reference to FIG. 1 the antimicrobial cap includes outer cap 100, inner component 200 and pad 300. Specifically, the pad 300 is disposed and secured within the chamber formed by the flexible arms 204 and 206 of the inner component 200. Furthermore, the inner component 200 engages the inner surface of the outer cap 100 using flexible legs 202. As a result, the outer cap 100, inner component 200 and the pad 300 are nested together before, during and after use.

Figure 8B:
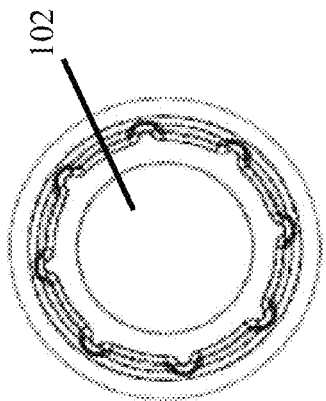
FIG. 8B is a top view of an antimicrobial cap in a ready-to-use position, in accordance with the disclosed subject matter.
Figure 8D:
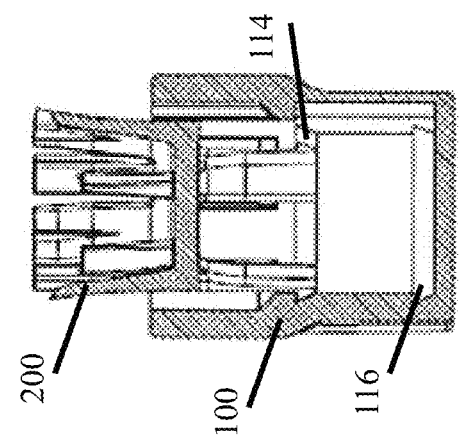
FIG. 8D is a side cross-sectional perspective view of an antimicrobial cap, in a ready-to-use position in accordance with the disclosed subject matter.
Figure 8A:
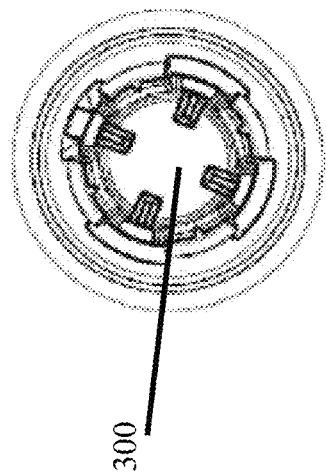
FIG. 8A is a bottom view of an antimicrobial cap in a ready-to-use position, in accordance with the disclosed subject matter.
Figure 8C:
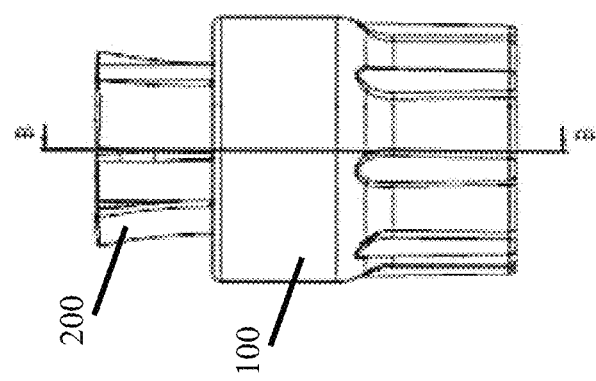
FIG. 8C is a side view of an antimicrobial cap in a ready-to-use position, in accordance with the disclosed subject matter.

FIGS. 8A-8D show various views and cross-sections of the assembled antimicrobial cap in accordance with some embodiments of the disclosed subject matter. Specifically, FIG. 8A shows a bottom view of the assembled antimicrobial cap illustrating the placement of pad 300 in the chamber formed by inner component 200. FIG. 8B shows a top view of assembled antimicrobial cap including closed end 102 of the outer cap 100. FIG. 8C is a side view of the assembled antimicrobial cap including outer cap 100, inner component 200 and cross-sectional lines B-B that are represented in FIG. 8D. FIG. 8D shows a side cross-sectional perspective view of the antimicrobial cap. As shown, the legs of inner component 200 are disposed within the cavity defined by outer cap 100 while the arms of inner component 200 are partially disposed outside the cavity defined by outer cap 100.

The antimicrobial cap has a first position whereby the flexible arms 206 and straight arms 208 are partially exposed outside the outer cap 100, and a second position whereby the flexible arms 206 and straight arms 208 are disposed inside the outer cap 100. Furthermore, when the antimicrobial cap is in the first position, the protrusions 204 of inner component 200 engage a first set of female depressions/grooves 114 can be located at diametrically opposite sides of the inner surface of outer cap 100 or that can be a radial depression about the inner circumference of the outer cap. In some embodiments, outer cap 100 includes a set of female depressions/grooves 114 located in the inner surface of outer cap 100 that is proximal to skirt 108 and a set of female depressions or grooves 116 located in the inner surface of outer cap 100 that is near closed end 102. Female depressions/grooves 114 and 116 allow inner component 200 to be securely attached when placed at different positions with respect to outer cap 100. The female depressions/grooves 114 and 116 can furthermore include a radial groove about the inner circumference of the outer cap.

Figure 9C:
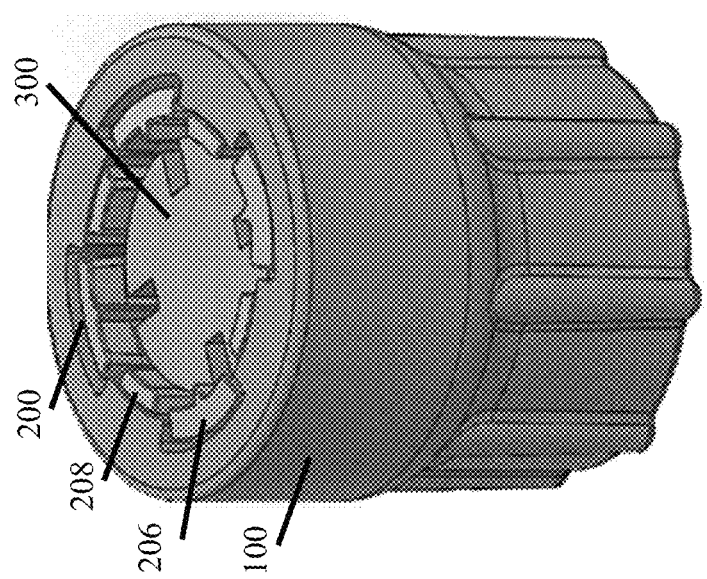
FIG. 9C is a side isometric view of the antimicrobial cap of FIG. 1 at a third position, in accordance with the disclosed subject matter.
Figure 9B:
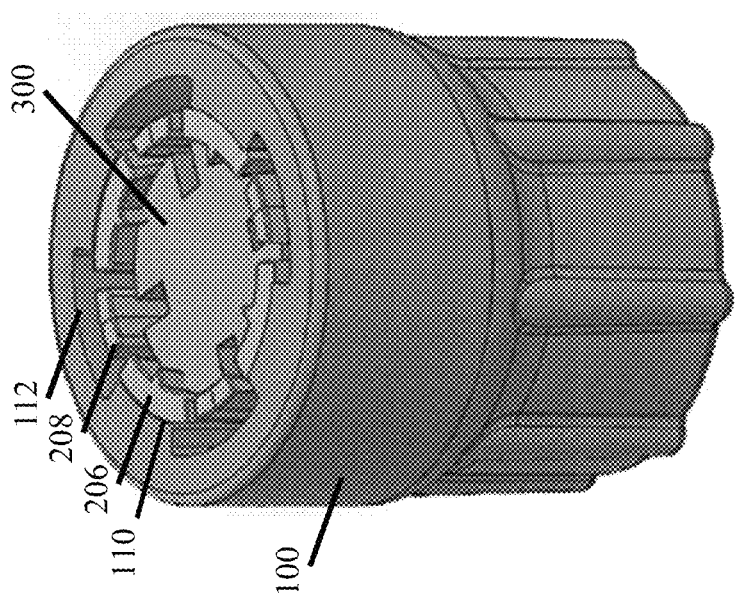
FIG. 9B is a side isometric view of the antimicrobial cap of FIG. 1 at a second position, in accordance with the disclosed subject matter.
Figure 9A:
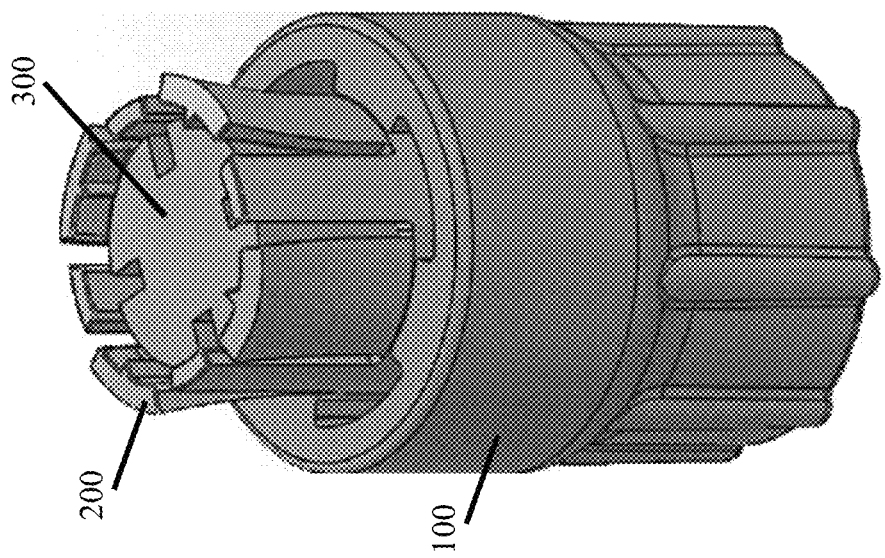
FIG. 9A is a side isometric view of the antimicrobial cap of FIG. 1 at a first position, in accordance with the disclosed subject matter.

Solely for purpose of illustration, reference is now made to FIGS. 9A-9C showing the assembled antimicrobial cap and the relative positioning of its components e.g., outer cap 100, inner component 200 and pad 300 during the different stages of its use for disinfecting a port. Specifically, FIG. 9A shows the assembled antimicrobial cap at its first position when removed from its packaging and prior to engaging a port. As discussed above in reference to FIGS. 9A-9C, in the first position, the pad 300 contains the antimicrobial agent is disposed in the chamber and is located at the proximal end of inner component 200. Moreover, the proximal end of inner component 200 is disposed outside the cavity defined by the inner surface of outer cap 100. On the other hand, the distal end of inner component 200 is disposed within the cavity such that protrusions 204 of legs 202 of inner component 200 engage the female depressions/grooves 114 located proximate the skirt 108. This positioning of inner component 200 with respect to outer cap 100 ensures that inner component 200 remains securely coupled to outer cap 100 and is visually in a ready position for a user in this embodiment. In addition, the inner component 200 is aligned with the outer cap 100 such that outwardly biased arms 206 are adjacent the abutment surfaces 110 and straight arms 208 are adjacent to longitudinal channels 112. In alternative embodiments with a flexible chamber at a portion of the proximal end and the arms at the remaining portion, the flexible chamber is adjacent the abutment surfaces and the longitudinal channels.

FIG. 9B shows the assembled antimicrobial cap at the second position, the position of use e.g., the position with the cap being attached to a port (not shown). Specifically, once a port engages the arms of inner component 200 placed in the manner discussed in reference to FIG. 9A, the cap can be pushed against the port to engage the port with the pad 300. Upon compressing the pad, the antimicrobial agent is released in order to disinfect the port and as a result, the port also pushes inner component 200 to move the inner component further into the cavity of the outer cap 100. After the movement of inner component 200 within the outer cap 100, the proximal end of the inner component can be at least further partially or entirely disposed within the cavity defined by the inner surface of outer cap 100. As such, the inner component 200 remains aligned with outer cap 100 such that outwardly biased flexible arms 206 are placed adjacent to abutment surfaces 110 and straight arms 208 are adjacent to longitudinal channels 112, as depicted in FIG. 9B. Accordingly, in this second position, the flexible arms 206 (previously in an outwardly biased state) are radially closer to a longitudinal center of the cap to facilitate engagement of the port, and can further assist to compress the pad 300 along a sidewall thereof to release antimicrobial agent therefrom. Similarly, the distal end of inner component 200 disposed within the cavity can transition the protrusions 204 of legs 202 of inner component 200 from the female depression/groove 114 and move towards the closed end of outer cap 100 to engage the groove 116 located near closed end 102. This positioning of inner component 200 with respect to outer cap 100 ensures that inner component 200 remains securely coupled to outer cap 100 during engagement to the port and use of the antimicrobial cap.

FIG. 9C shows the assembled antimicrobial cap and its components e.g., outer cap 100, inner component 200 and pad 300 at a third position, a position post-use for disinfecting a port and upon disengagement of the port. As discussed above in reference to FIG. 9A, initially the antimicrobial cap is at a first position. Once the cap has engaged the port and has pushed inner component 200 into the cavity of outer cap 100 as discussed above in connection to FIG. 9B, the cap is at a second position. The inner component 200 can then be rotatable with respect to outer cap 100, as discussed above in connection to FIG. 9C, where the cap can be placed in a third position, the disengagement position. For example, once legs 202 of inner component 200 reach the closed end of outer cap 100 and engage groove 116 located near closed end 102 of outer cap 100, then the inner component 200 can rotate with respect to outer component 100 to cause the outwardly biased arms 206 to move radially to align with and be housed within the longitudinal channels 112. As a result, outwardly biased arms 206 engage and lock into longitudinal channels 112 thus inhibiting additional movement of inner component 200 with respect to outer cap 100. Similarly, straight arms 208 move radially and are aligned with the abutment surfaces 110, as shown in FIG. 9C. Such movement causes the port to become disengaged from the antimicrobial cap indicating that the port has been disinfected as the biasing or engagement arms are no longer biased against the port. In some embodiments, longitudinal channels 112 of outer cap 100 have the same or larger width than outwardly biased arms 206 to allow for secure coupling e.g., locking of the two. In some embodiments, rotation of inner component 200 with respect to outer cap 100 can be bidirectional, counterclockwise and/or clockwise and disengagement of the port can occur after any suitable number of revolutions of inner component 200 with respect to outer cap 100.

Once the cap has been disengaged from the port, the inner component 200 remains securely disposed within the cavity of outer cap 100 and further axial movement in any direction is inhibited. As a result, antimicrobial cap 10 provides a lockout mechanism that disables the cap from future use, thus preventing reapplication to the port. As such, the antimicrobial cap can be, and is preferably, configured as a single-use cap. After the antimicrobial cap 10 is removed from a port, re-use of the antimicrobial cap 10, including non-compliant re-use, can be prevented. In some cases, such re-use of the antimicrobial cap can be in violation of industry and regulatory standards to ensure proper disinfection. For example, after a first use, the antimicrobial cap can become less effective due to exposure to the external environment, which can contaminate the cap and/or dry out antiseptic solution contained in the cap and thus can render the cap ineffective. Accordingly, the antimicrobial cap 10 can be, and is preferably, configured to prevent these and other risks associated with re-use activities.

Figure 10A:
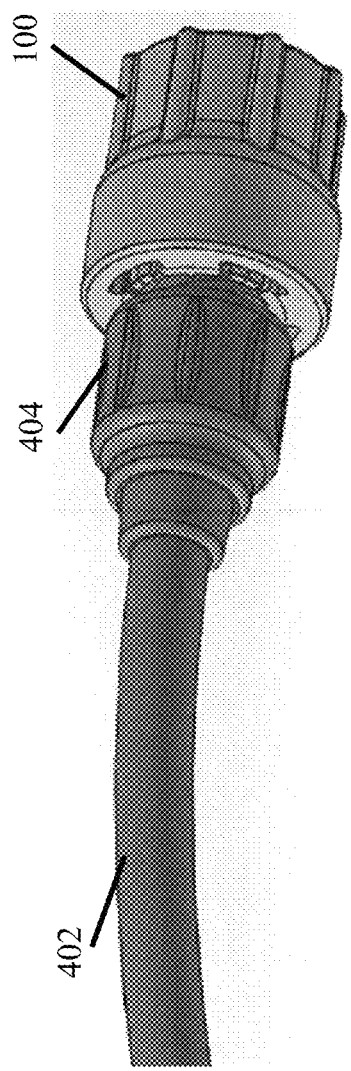
FIG. 10A is a side isometric view of the antimicrobial cap of FIG. 1 engaging a medical port, in accordance with the disclosed subject matter.
Figure 10C:
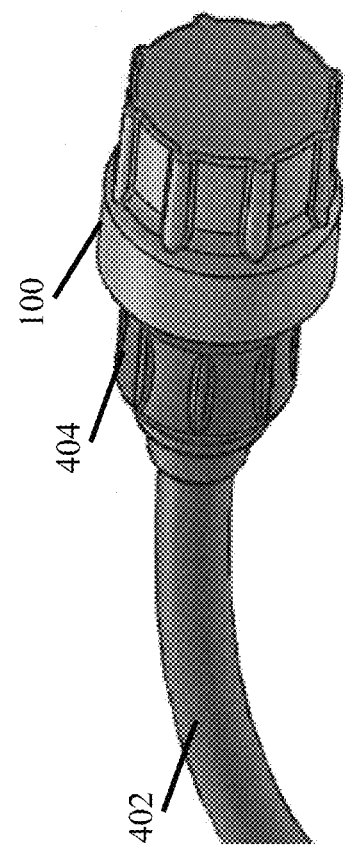
FIG. 10C is an isometric view of the antimicrobial cap of FIG. 1 engaging a medical port, in accordance with the disclosed subject matter.
Figure 10B:
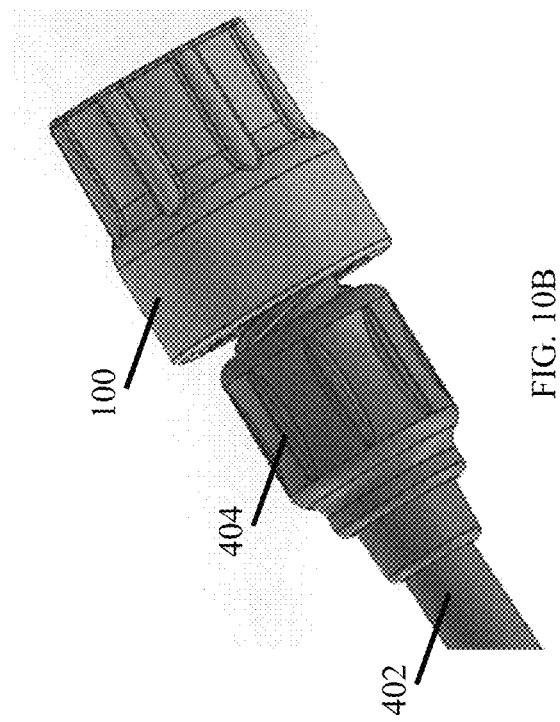
FIG. 10B is a side view of the antimicrobial cap of FIG. 1 engaging a medical port, in accordance with the disclosed subject matter.

FIGS. 10A-10C show different views of assembled antimicrobial cap engaging a port for disinfection. FIG. 10A shows a side view of line 402 connected to port 404 engaging the assembled antimicrobial cap and pushing inner component 200 into the cavity of outer cap 100. FIG. 10B shows an elevated side view of port 404 engaging the antimicrobial cap during the disinfection process. FIG. 10C shows a front view of line 402 connected to port 404 engaging the antimicrobial cap during the disinfection process.

Figure 11B:
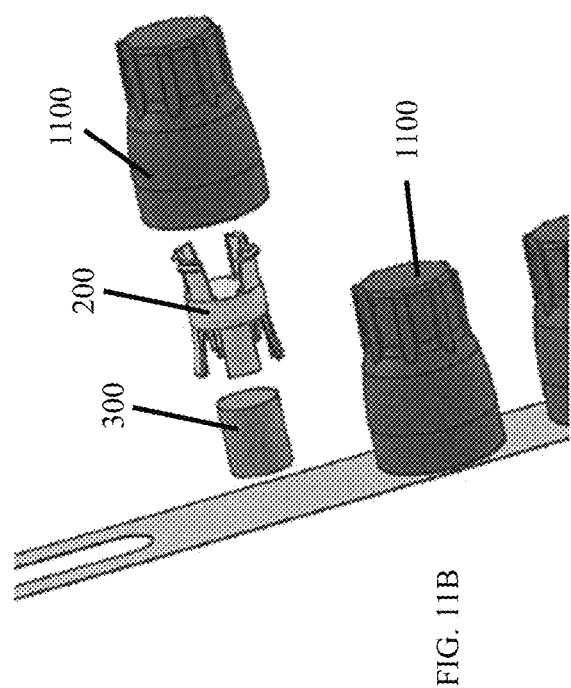
FIG. 11B is an exploded view of the antimicrobial cap of FIG. 11A engaging a foil laminate packaging strip, in accordance with the disclosed subject matter.
Figure 11A:
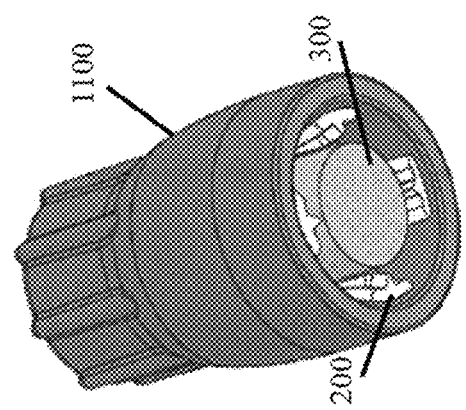
FIG. 11A is a bottom perspective view of an alternate embodiment of the antimicrobial cap, in accordance with the disclosed subject matter.
Figure 11C:
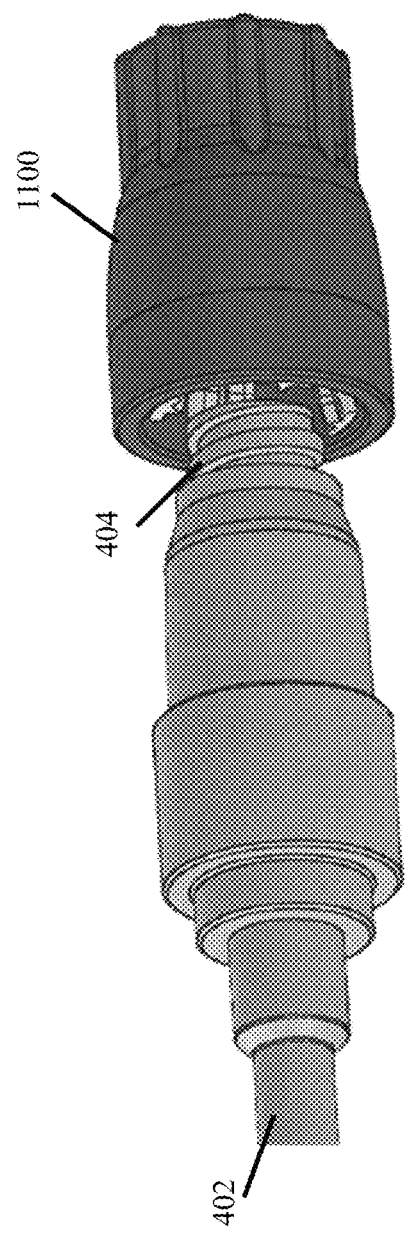
FIG. 11C is a side view of the antimicrobial cap of FIG. 11A engaging a medical port, in accordance with the disclosed subject matter.

FIGS. 11A-11C show an alternate embodiment of the assembled antimicrobial cap as attached to a packaging unit (FIG. 11B), as removed from the packaging unit (FIG. 11A), and as used with a port (FIG. 11C). As shown in FIG. 11A, the antimicrobial cap includes outer cap 1100, inner component 200 and pad 300. Specifically, in this embodiment, outer cap 1100 includes an extended outer cap sidewall such that the sidewall encloses the inner component 200 and extends beyond a proximal end of the inner component 200. In some embodiments the extended outer cap 1100 can be sealed to a packaging element, such as a foil strip (as shown in FIG. 11B) or a lid 304 for transportation and storage purposes. In some embodiments, use of the extended outer cap 1100 can eliminate the need for additional secondary packaging, such as housing 302. In other embodiments, the antimicrobial cap of FIG. 11B can further be housed within housing 302, or alternatively the antimicrobial cap can be packaged with a lid 304 without a housing 302 to enable the extended outer cap to be directly coupled with the lid 304, as shown in FIG. 11B. In FIGS. 11A and 11C, the cap is at a first position when removed from the packaging unit and prior to engaging the port 404.

As discussed above, in the first position, the pad 300 contains the antimicrobial agent that is disposed in the chamber and is located at the proximal end of inner component 200. Moreover, the proximal end of inner component 200 is disposed inside the cavity defined by the inner surface of the extended outer cap 1100. Similarly, the distal end of inner component 200 is disposed within the cavity such that protrusions 204 of legs 202 of inner component 200 engage the female depressions/grooves 114 and 116 located proximate the skirt 108. This positioning of inner component 100 with respect to the extended outer cap 1100 ensures that inner component 200 remains securely coupled to outer cap 1100. In addition, the inner component 200 is aligned with the extended outer cap 1100 such that outwardly biased arms 206 are adjacent the abutment surfaces 110 and straight arms 208 are adjacent to longitudinal channels 112.

FIG. 11C shows a side view of line 402 connected to port 404 engaging the antimicrobial cap including the extended outer cap 1100 during the disinfection process. In some embodiments, inner component 200 remains disposed within the extended outer cap 1100 prior, during and after being connected to port 404.

Figure 12:
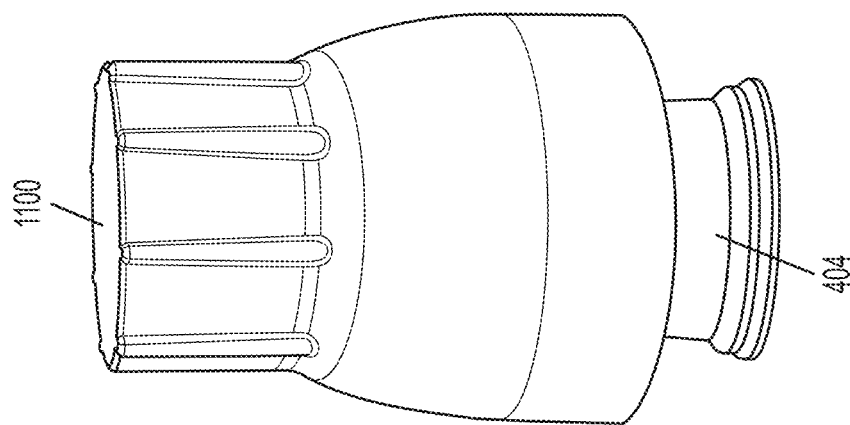
FIG. 12 is a side view of exemplary outer caps for the antimicrobial cap, in accordance with the disclosed subject matter.
Figure 12:
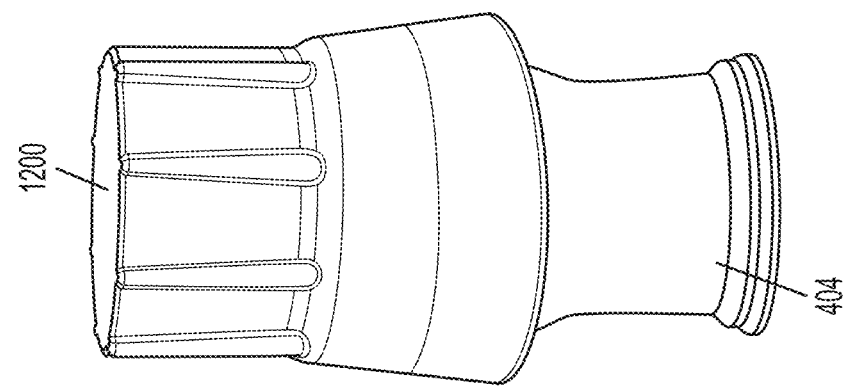
Figure 12:
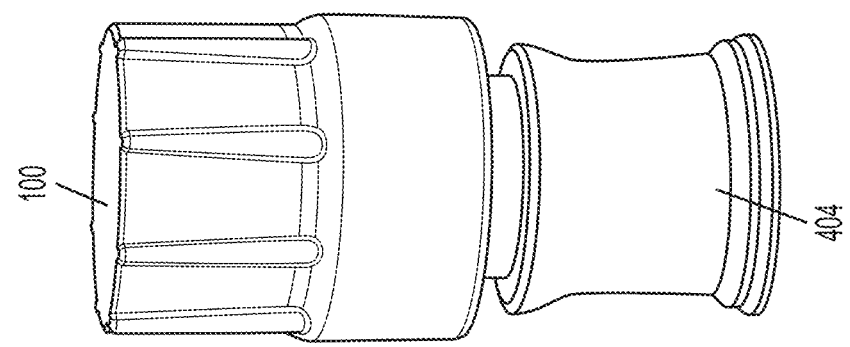

FIG. 12 shows a side perspective view of exemplary embodiments of outer caps included as part of the antimicrobial cap that are coupled with a distal end of a port 404. For example, in some embodiments, the outer cap 100 can be used as an overcap to inner component 200 and pad 300 without an additional housing 302 as discussed herein with respect to FIG. 13 to enable attachment to a packaging element 304. As such, the outer cap 100 can at least partially enclose inner component 200. In other embodiments, the antimicrobial cap can include a different packaging mechanism such as a blister pack, as depicted in FIG. 15C, or blister strip, as depicted in FIG. 15F. As shown in FIG. 15F, an outer cap 1200 can be structured to couple with a blister package. In such embodiments, the blister outer cap 1200 can have a skirt 108 with a perimeter that can enclose port 404 during use of the antimicrobial cap, as further discussed herein with respect to FIG. 15F. Furthermore, in some embodiments, the antimicrobial cap can include the extended cap 1100 such that a sidewall of the cap fully encloses the inner component 200 during the different stages of its use for disinfecting a port, as previously described with respect to FIG. 11A. The extended cap 1100 can be packaged directly on strip, as depicted in FIG. 11B, or on a lid 304, such as that depicted in FIG. 14B. The extended cap 1100 can be attached to a strip or lid on an outer rim of the extended cap 1100 as described further herein. Alternatively, the antimicrobial cap can be packaged in a sleeve dispenser as further described herein with respect to FIG. 15E. The outer cap 100, blister outer cap 1200 and extended outer cap 1100 can be suitably packaged as desired, and can comprise plastic, polymer (e.g., HDPE), silicone or any other suitable material that can be molded, cast and/or manufactured using 3D printing.

Figure 13:
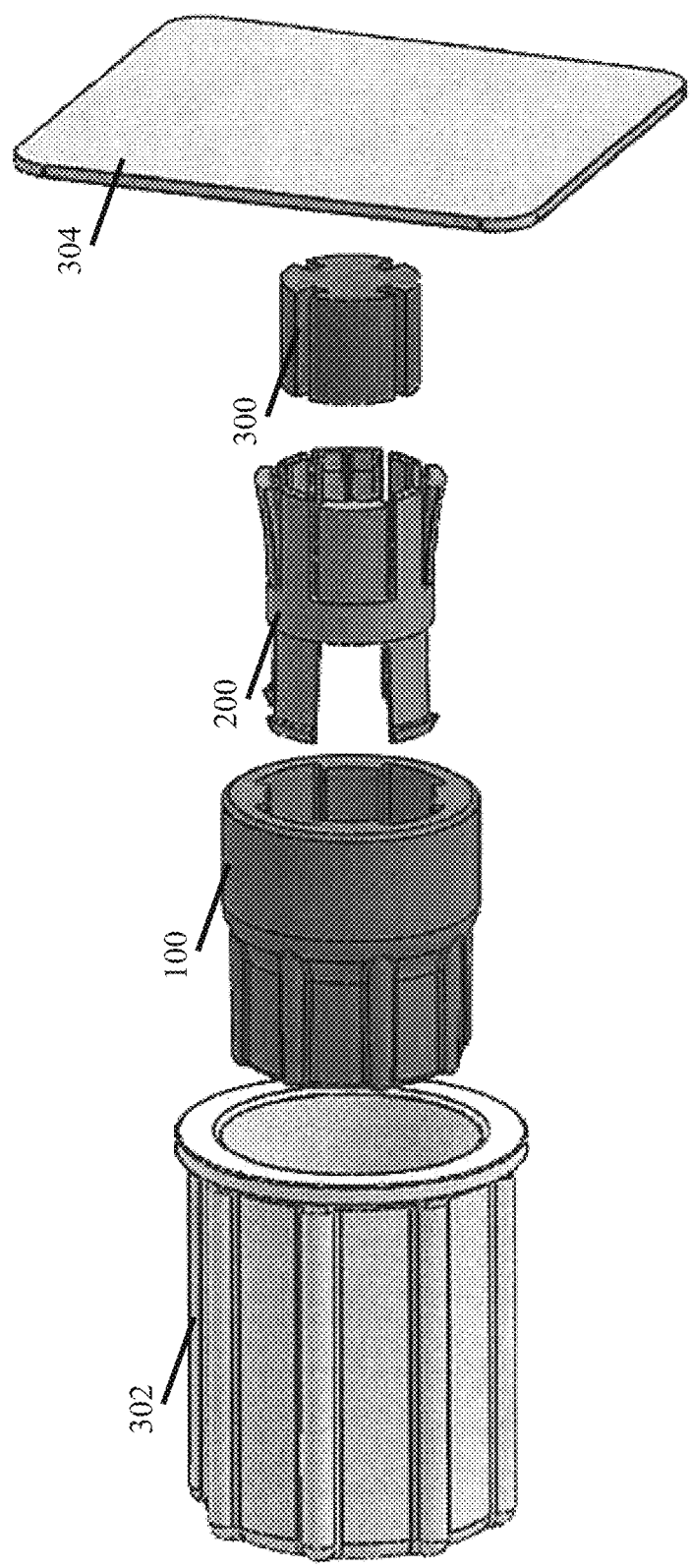
FIG. 13 is an exploded view of the antimicrobial cap of FIG. 1 in an outer housing package or cap as a single packaged embodiment, in accordance with the disclosed subject matter.

Solely for purpose of illustration, reference is now made to FIG. 13 showing an exploded side view of the antimicrobial cap 10 with a housing and lid. Specifically, the antimicrobial cap can be disposed within a chamber defined by housing 302. The chamber is sealed using lid 304 that is placed on the rim of housing 302. In some embodiments, the housing 302 is made out of rigid material and has a diameter larger than the outermost diameter of the antimicrobial cap's outer cap 100. In some embodiments, the housing 302 can be made using flexible material that is capable to stretch and expand in order to enclose the antimicrobial cap. The antimicrobial cap is assembled by disposing pad 300 that contains the antimicrobial agent into the chamber formed by the flexible arms in the proximal end of inner component 200. Subsequently, the flexible legs in the distal end of inner component 200 engage and couple to the engagement structure disposed in the inner surface of outer cap 100. In some embodiments, inner component 200 is partially disposed within outer cap 100 such that the flexible arms are located outside outer cap 100 so as to engage the port. In such assembled position, the antimicrobial cap is packaged using housing 302 and lid 304 and can be transported/shipped in a ready to use state.

Figure 14B:
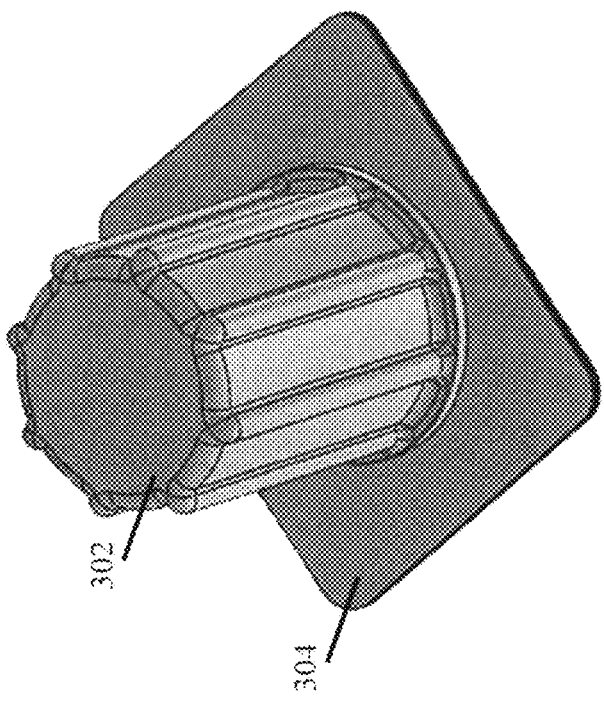
FIG. 14B is a top perspective view of the packaging of FIG. 14A, in accordance with the disclosed subject matter.
Figure 14C:
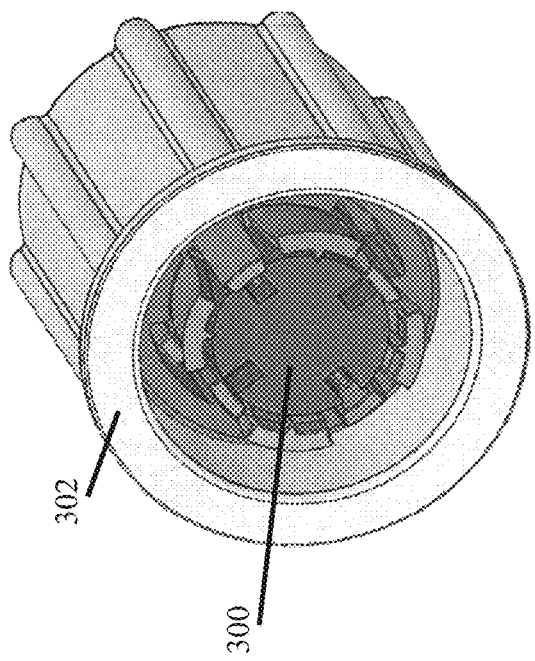
FIG. 14C is a bottom perspective view of a portion of the packaging of FIG. 14B in accordance with the disclosed subject matter.
Figure 14A:
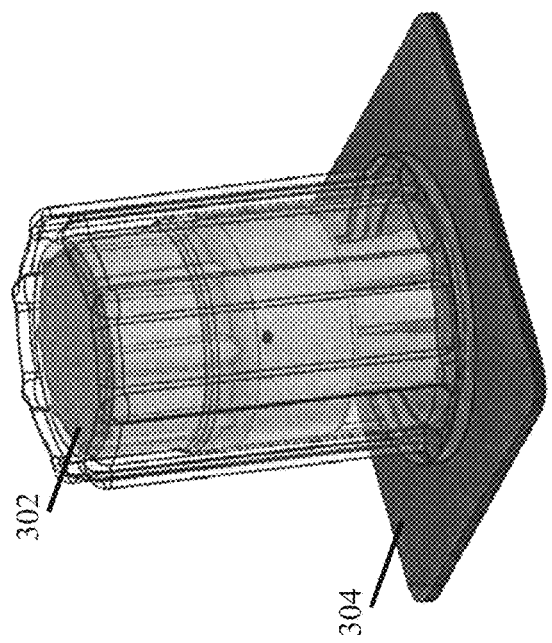
FIG. 14A is a side perspective view of a packaging shown in phantom lines for the antimicrobial cap of FIG. 1, in accordance with the disclosed subject matter.

Solely for purpose of illustration, reference is now made to FIGS. 14A-14B showing side perspective views of the packaging with the antimicrobial cap in phantom and without phantom, respectively. Specifically, upon manufacturing and prior to use, the antimicrobial cap 10 is provided with individual packaging to ensure that it is sealed from the external environment and not exposed to contamination elements. For example, as shown in FIGS. 14A-14B packaging of the antimicrobial cap includes a housing 302 that has an open end and a closed end that defines a chamber of a generally cylindrical shape such that it can fully enclose the antimicrobial cap and provide a sterile environment. Furthermore, housing 302 has an external surface that can include any suitable structure that allows for ease of use and removal of the antimicrobial cap from the packaging. In order to seal the chamber and antimicrobial cap disposed therein, the packaging also includes lid 304 that is coupled to the rim of housing 302. Lid 304 can be made out of a plurality of materials such as plastic, aluminum, a laminate combination, or any other suitable material.

FIG. 14C shows antimicrobial cap 10 disposed within housing 302 upon removal of lid 304, as described in some embodiments of the disclosed subject matter. As shown, the housing 302 fully encloses the antimicrobial cap such that no part of outer cap 100, inner component 200 and pad 300 is exposed to the external environment. In some embodiments, the antimicrobial cap can be used to engage and disinfect a port with or without housing 302 attached. Housing 302 can be made with any suitable material. For example, housing 302 can be made out of plastic, polymer (e.g., PE), silicone or any other suitable material that can be molded, cast and/or manufactured using 3D printing.

Figure 15B:
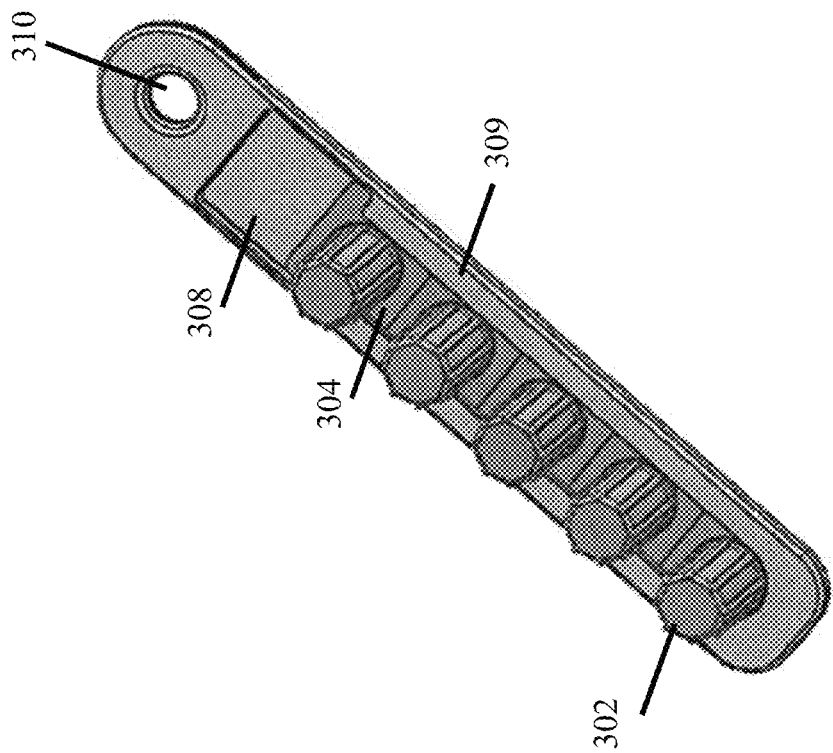
FIG. 15B is a top perspective view of a rigid packaging for a plurality of antimicrobial caps, in accordance with an alternate embodiment.
Figure 15A:
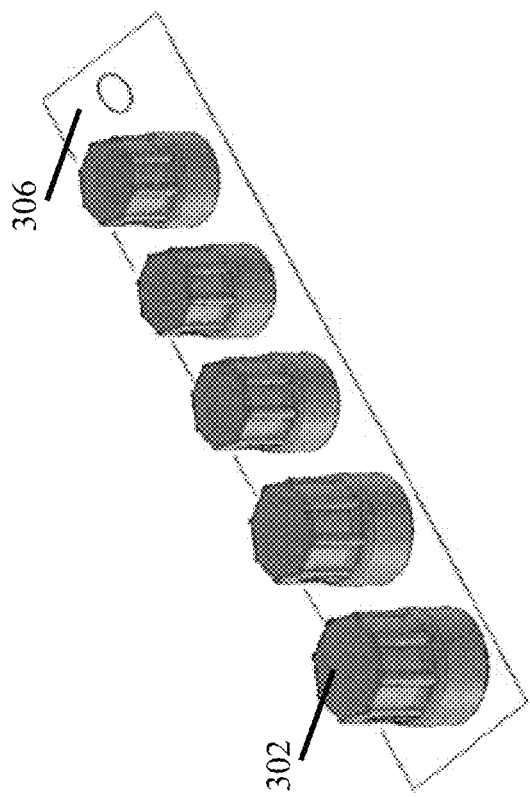
FIG. 15A is a top perspective view of a flexible strip packaging for a plurality of antimicrobial caps, in accordance with the disclosed subject matter.
Figure 15F:
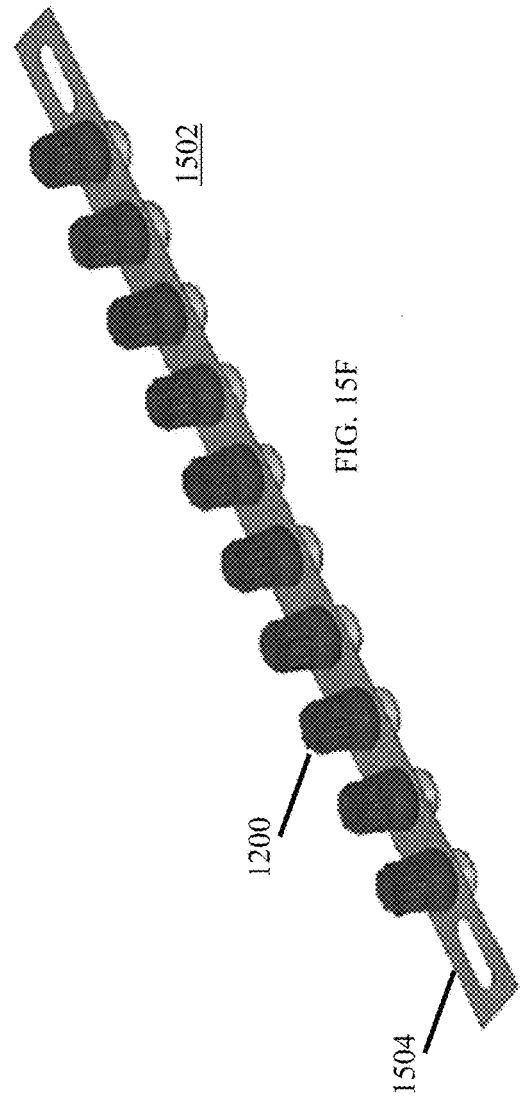
FIG. 15F is a side perspective view of a flexible strip packaging for a plurality of antimicrobial caps, in accordance with an alternate embodiment.

FIGS. 15A-15D illustrate alternative packaging components for a plurality of antimicrobial caps in accordance with some embodiments of the disclosed subject matter. Specifically, FIG. 15A shows a plurality of antimicrobial caps each of them enclosed in housing 302 and sealed using strip 306. In some embodiments, housing 302 can be extended cap 1100 or any other suitable housing and/or cap. In some embodiments, the seal 306 can provide an adhesive to ensure that the antimicrobial caps are securely placed on strip 306 and hermetically sealed from the external environment. In some embodiments, the seal 306 can be a foil/aluminum seal and include a hole for hanging/storage purposes. In addition, FIG. 15B shows a plurality of antimicrobial caps each of them enclosed in housing 302 and sealed using the lid 304. Each cap with its lid can be positioned upon a rigid strip 308 and inserted within a guide structure 309 defining a longitudinal channel that allow for an individually packaged antimicrobial cap e.g., referenced in connection with FIGS. 13, 14A, 14B and 14C to slide off the strip 308. The strip can further define an opening 310 so that the strip can be conveniently located. In some embodiments, the strip 308 can be made out of plastic, polymer (e.g., PC, ABS), silicone or any other suitable rigid material that can be molded, cast and/or manufactured using 3D printing.

Figure 15H:
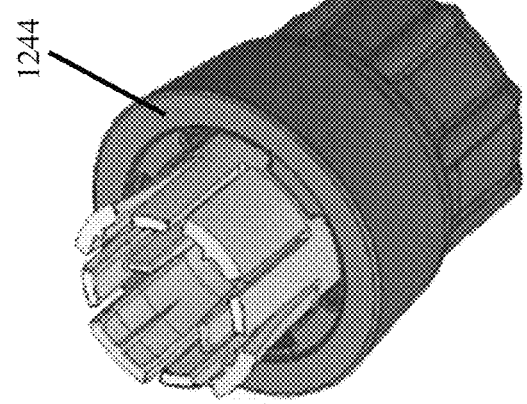
FIG. 15H is a side perspective view of the antimicrobial cap of FIG. 15F without the packaging portion in accordance with the disclosed subject matter.
Figure 15G:
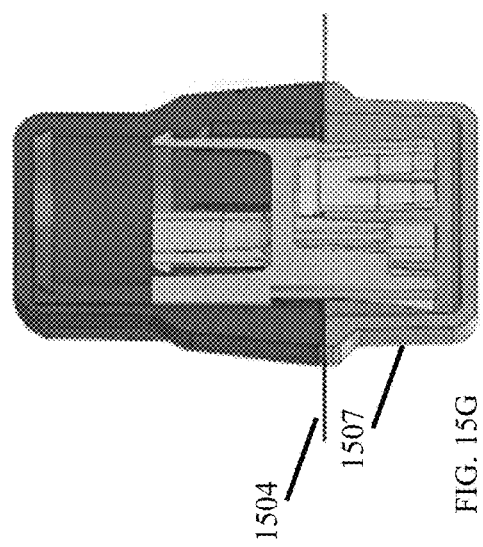
FIG. 15G is a side cross-sectional view of a portion of the flexible strip packaging and antimicrobial cap of FIG. 15F, in accordance with the disclosed subject matter.

FIG. 15C shows a plurality of antimicrobial caps each of them individually enclosed in blister pack 1502 and sealed using strip 1504. In some embodiments, the antimicrobial caps can include extended outer cap 1100, as previously described. Extended outer cap 1100 can protect inner component 200 during transportation and storage as well as during extraction of the antimicrobial cap from the blister pack. In some embodiments, the seal 1504 can be a foil/aluminum seal such that the antimicrobial caps can be dispensed from the blister pack 1502 and can include a hole 1503 for hanging/storage purposes. FIGS. 15F-15H show an alternate embodiment of a blister pack 1502 in which a rim 1244 of the blister outer cap 1200 is sealed to a strip 1504 that includes recessed containers 1507 that can house the proximal end of the cap 10 therein. Recessed containers 1507 can be made of a suitably rigid material so as to protect the inner component 200 during transportation and storage.

Figure 15K:
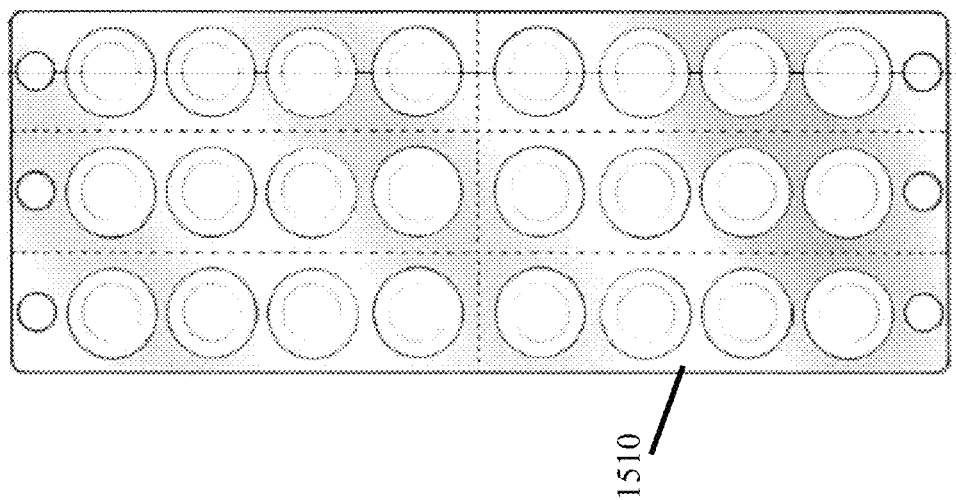
FIG. 15K is a perspective view of a plurality of packages of FIG. 15I, in accordance with the disclosed subject matter.
Figure 15J:
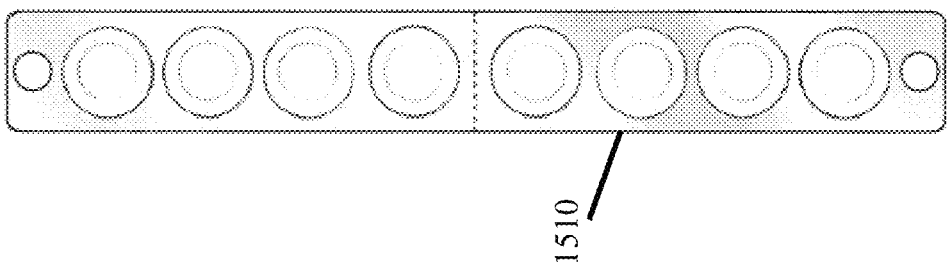
FIG. 15J is a perspective view of a configurable strip packaging for a plurality of antimicrobial caps of FIG. 11A viewed from the top of the plurality of caps, in accordance with an alternate embodiment.
Figure 15I:
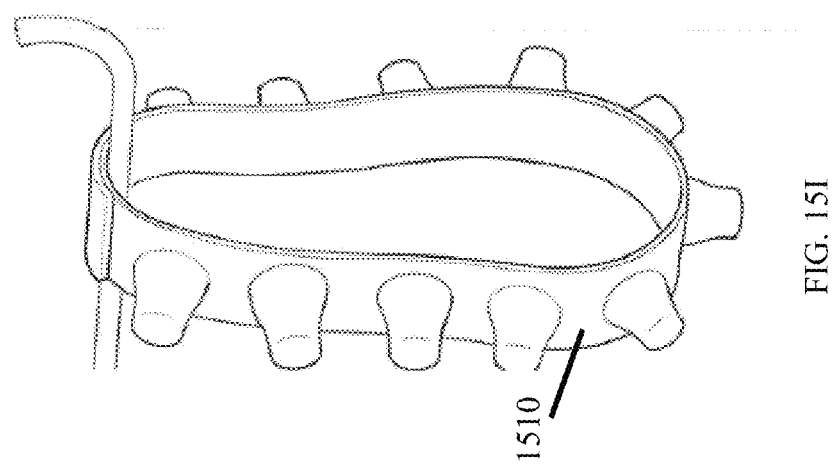
FIG. 15I is a side perspective view of a flexible strip packaging for a plurality of antimicrobial caps of FIG. 11A, in accordance with an alternate embodiment.

FIG. 15E shows an isometric side perspective view of an alternate packaging for a plurality of antimicrobial caps 10. Specifically, the packaging includes a dispenser sleeve 1506 that is capable of dispensing the antimicrobial caps 10 from nozzle 1508. Furthermore, the antimicrobial caps 10 of FIG. 15E can be sealed onto each other in the dispenser sleeve, such that a pull motion to the bottom antimicrobial cap also unseals the cap. In further embodiments, the antimicrobial caps 10 can remain individually sealed when dispensed by dispenser sleeve 1506. In some embodiments, the dispenser or packaging can hang straight from an IV pole for ease of access, as shown in FIG. 15I. Additional configurations of strips are shown in FIGS. 15J and 15K. In FIG. 15J, a strip of four caps is coupled to a second strip of four caps by a perforation line. FIG. 15K depicts a series of strips coupled together about perforation lines. The number of caps per strip can vary as desired.

The antimicrobial element contained within the pad can be suitable for any medical application. For instance, the fluid medium contained within the pad can be an antiseptic solution, and application of the solution to a portion of a port can kill microorganisms. In one embodiment, application of the antiseptic solution can kill microorganisms immediately and within approximately 10 minutes and further have a persistent effect for at least 7 hours. In some embodiments, the antiseptic solution can comprise at least one of chlorhexidine gluconate (CHG), isopropyl alcohol, purified water, and mixtures thereof. In another embodiment, the antiseptic solution can comprise at least 3.15% w/v chlorhexidine gluconate and 70% v/v isopropyl alcohol (both ±10% w/v). The CHG can be designated as: 1,1'-hexamethylenebis [5-(p-chlorophenyl)biguanide] digluconate, and have the following chemical structure:

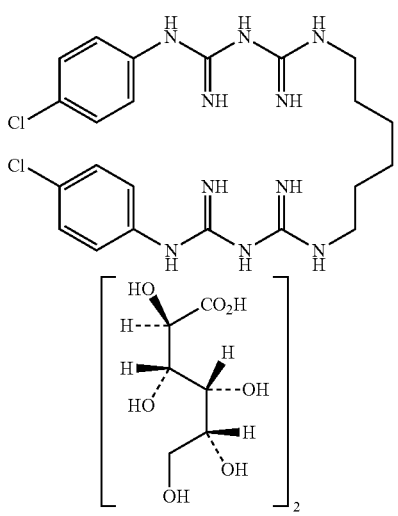

In accordance with another aspect of the disclosed subject matter, a method of inhibiting the growth and disinfecting a port is provided. Specifically, the disclosed subject matter comprises providing an antimicrobial cap having outer cap 100, inner component 200 and pad 300 disposed within a chamber of the inner component that is impregnated with an antimicrobial element such as, for example, a disinfecting solution. The anti-microbial cap is used to clean and/or disinfect various medical ports that are used for treatment. In some embodiments, the antimicrobial element includes a solution such as alcohol, chlorhexidine gluconate and/or mixtures such as chlorhexidine-silver or any suitable combination thereof.

Moreover, the outer cap has a closed end and an open end that defines a cavity. The cavity has a sidewall with an inner surface that includes an engagement structure. The engagement structure includes alternating longitudinal channels 112 and abutment surfaces 110 that engage the inner component of the antimicrobial cap. The inner component, which is receivable in the outer cap, has a distal end that includes a first attachment member such as one or more legs 202 that engage with the outer cap and a proximal end that includes a second attachment member such as arms 206 and arms 208. Initially, the second attachment member of the inner component is at least partially disposed outside the cavity of the outer cap in a first position and subsequently the inner component is axially movable such that the second attachment member of the inner component is at least partially disposed inside the cavity of the outer cap in a second position.

Furthermore, once the port is engaged to the antimicrobial cap in the second position, the outer cap becomes rotatable with respect to the inner component. Such movement allows for the inner component's attachment member to lock in the outer cap thus disengaging the port from the antimicrobial cap while the inner component remains coupled within the cavity of the outer cap upon the disengagement of the port, in the third position.

Figure 16:
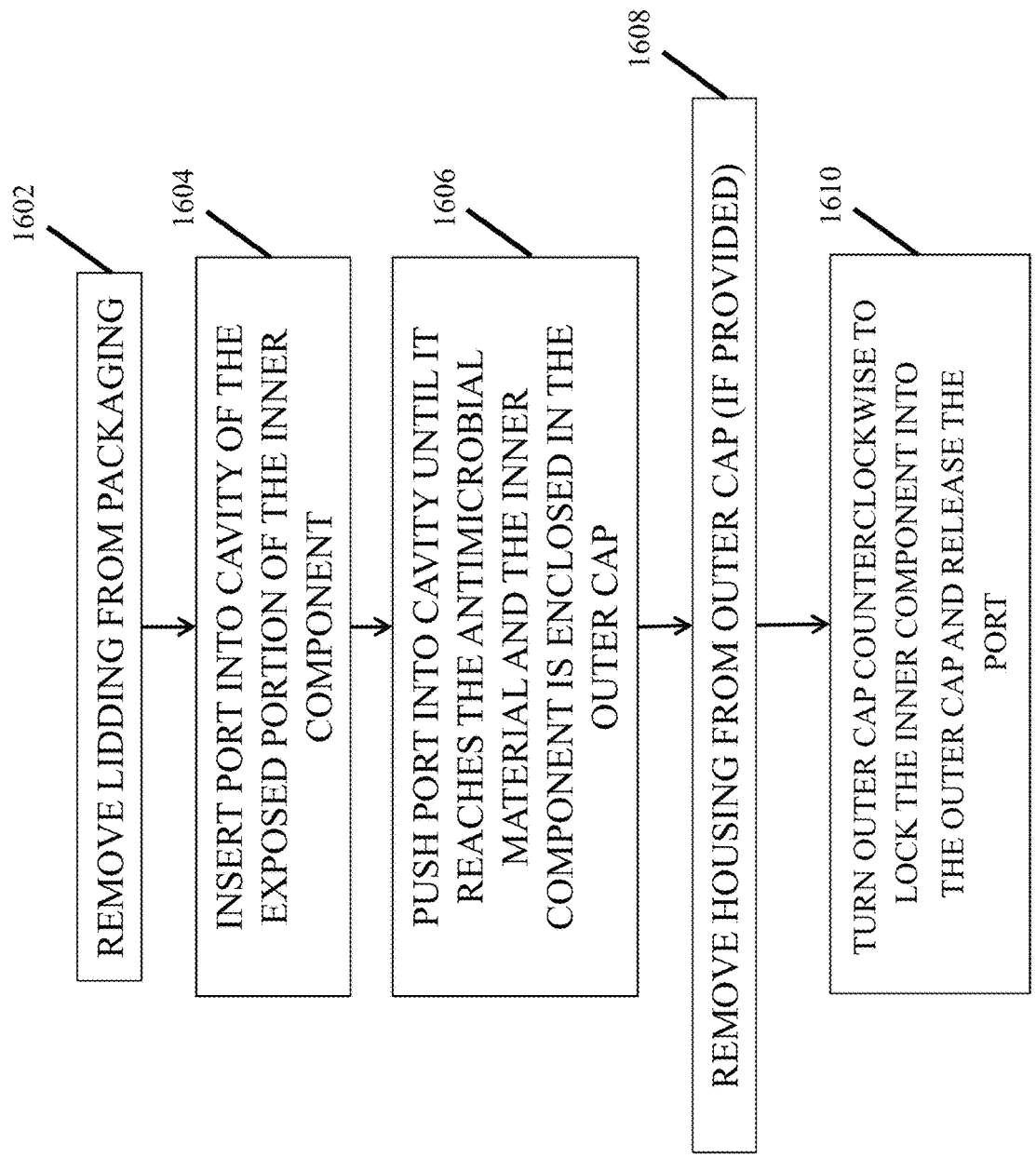
FIG. 16 illustrates a process for disinfecting a port using the antimicrobial cap of FIG. 1, in accordance with the disclosed subject matter.

FIG. 16 illustrates a process diagram for inhibiting the growth of microbes and disinfecting a port using antimicrobial cap 10 in accordance with embodiments of the disclosed subject matter. Specifically, the packaging lid 304 is removed to uncover the antimicrobial cap at 1602. At 1604, the port is inserted in the exposed portion of inner component 200 subsequently, at 1606, the port is pushed (e.g., axially moved) into the cavity of outer cap 100 (or the cap is pushed onto the port) until the port reaches pad 300 and is coupled within the inner component as both become enclosed within outer cap 100. At 1608, the housing 302 (if provided) is removed uncovering cap 10 attached to a port. Finally, at 1610, turning the port rotationally (counterclockwise by half a turn) causes outer cap 100 to rotate with respect to inner component 200 and release the port. This is achieved by having longitudinal channels 112 move radially until aligned with the outwardly biased port attachment arms 206. As a result, outwardly biased arms 206 engage and lock into longitudinal channels 112 thus preventing additional movement of inner component 200 with respect to outer cap 100. Similarly, straight arms 208 move laterally and become aligned to abutment surfaces 110. Such movement causes the antimicrobial cap 10 to become disengaged from the port, indicating that the port has been disinfected, while disabling the antimicrobial cap and preventing its reapplication. As such, and as previously described herein, the antimicrobial cap 10 can be configured as a single-use cap.

While the disclosed subject matter is described herein in terms of certain preferred embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the various embodiments depicted and claimed, the disclosed subject matter is also directed to other embodiments having any other possible combination of the features disclosed and claimed herein. As such, the particular features presented herein can be combined with each other in other manners within the scope of the disclosed subject matter such that the disclosed subject matter includes any suitable combination of the features disclosed herein. Furthermore, although reference is made to a port throughout this disclosure, other suitable devices and connectors likewise can be disinfected using the antimicrobial cap and method disclosed herein. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method of the disclosed subject matter without departing from the spirit or scope of the disclosed subject matter. Thus, it is intended that the disclosed subject matter include modifications and variations that are within the scope of the appended claims and their equivalents.

What is claimed is:

1. An antimicrobial cap to treat a port, the antimicrobial cap comprising:
    an outer cap having an open end, a closed end and defining a cavity therein, the outer cap having a sidewall with an inner surface that defines an engagement structure;
    an inner component receivable in the outer cap, the inner component having a distal end comprising a first attachment member that engages with the engagement structure of the outer cap and a proximal end comprising a second attachment member to engage the port, wherein the proximal end of the inner component is aligned with a proximal end of the outer cap in a first position, and the second attachment member is at least partially disposed within the cavity of the outer cap in a second position, the inner component being axially movable from the first position to the second position with respect to the outer cap, and the outer cap being rotatable with respect to the inner component; and a pad disposed within a chamber of the inner component, the pad impregnated with an antimicrobial element, wherein the port is receivable in the chamber as the second attachment member engages an external surface of the port, the pad being compressed by the port to release the antimicrobial element therefrom when the inner component moves from the first position towards the second position to engage the inner component to the port, wherein the outer cap is rotatable about the inner component to a third position to disengage the inner component from the port such that the inner component remains coupled within the cavity of the outer cap upon disengagement.

2. The antimicrobial cap of claim 1, wherein the engagement structure of the outer cap comprises alternating longitudinal channels and longitudinal abutment surfaces disposed about the inner surface of the outer cap, and wherein the second attachment member comprises outwardly biasing arms, wherein the arms engage the longitudinal abutment surfaces in the first position to permit axial movement of the inner component with respect to the outer cap.

3. The antimicrobial cap of claim 1, wherein the first attachment structure includes legs and the engagement structure includes at least a first protrusion and a second protrusion distal from the first protrusion, wherein legs are engaged with the first protrusion in the first position and the legs are engaged with the second protrusion in the second position.

4. The antimicrobial cap of claim 1 further comprising:
a housing having an open end, a closed end and defining a chamber therein, wherein the housing encloses the outer cap within the chamber; and
a lid coupled to a rim of the housing to seal the chamber from an external environment.

5. The antimicrobial cap of claim 4, wherein the outer cap includes one or more projections on an exterior thereof configured to engage the housing.

6. The antimicrobial cap of claim 1, wherein the inner component comprises one or more posts extending from the chamber configured to secure the pad.

7. The antimicrobial cap of claim 6, wherein the pad comprises a foam having one or more grooves configured to be aligned with the one or more posts.

8. The antimicrobial cap of claim 1, wherein the first attachment member comprises at least four legs.

9. The antimicrobial cap of claim 1, wherein the second attachment member comprises at least four outwardly biasing arms and four arms extending uniformly in a single direction.

10. The antimicrobial cap of claim 1, wherein the antimicrobial element comprises alcohol, chlorhexidine gluconate, chlorhexidine-silver or mixtures thereof.

11. The antimicrobial cap of claim 1, wherein the first attachment member and the second attachment member of the inner component comprise molded flexural attachments.

12. The antimicrobial cap of claim 1, wherein the outer cap is configured to be rotated to the third position with respect to the inner component when engaged to the port causing release of the second attachment member from the port.

13. The antimicrobial cap of claim 12, wherein the outer cap is rotated causing the first attachment member of the inner component to be aligned with the engagement structure of the outer cap.

14. A method for inhibiting the growth of microbes and disinfecting a port, the method comprising:
providing an outer cap having an open end, a closed end and defining a cavity therein, the outer cap having a sidewall with an inner surface that defines an engagement structure, an inner component receivable in the outer cap, the inner component having a distal end comprising a first attachment member that engages with the engagement structure of the outer cap and a proximal end comprising a second attachment member to engage the port, wherein the proximal end of the inner component is aligned with a proximal end of the outer cap in a first position, and the second attachment member is at least partially disposed within the cavity of the outer cap in a second position, the inner component being axially movable from the first position to the second position with respect to the outer cap, and the outer cap being rotatable with respect to the inner component,
a pad disposed within a chamber of the inner component, wherein the inner component comprises one or more posts extending from the chamber configured to secure the pad, the pad impregnated with an antimicrobial element;
receiving the port in the chamber as the second attachment member engages an external surface of the port;
moving the inner component from the first position towards the second position to engage the inner component to the port;
compressing the pad with the port to release the antimicrobial element therefrom; and
rotating the outer cap about the inner component to a third position to disengage the inner component from the port such that the inner component remains coupled within the cavity of the outer cap upon disengagement.

15. The method of claim 14 further comprising:
providing a housing having an open end, a closed end and defining a chamber therein, wherein the housing encloses the outer cap within the chamber; and a lid coupled to a rim of the housing to seal the chamber from an external environment; and
removing the lid from the rim of the housing.

16. The method of claim 14, wherein the antimicrobial element comprises alcohol, chlorhexidine gluconate, chlorhexidine-silver or mixtures thereof.

17. An antimicrobial cap to treat a port, the antimicrobial cap comprising:
an outer cap having an open end, a closed end and defining a cavity therein, the outer cap having a sidewall with an inner surface that defines an engagement structure;
an inner component receivable in the outer cap, the inner component having a distal end comprising an attachment member that engages with the engagement structure of the outer cap and a proximal end comprising a flexible chamber to engage the port, wherein the proximal end of the inner component is aligned with a proximal end of the outer cap in a first position, and the flexible chamber is at least partially disposed within the cavity of the outer cap in a second position, the inner component being axially movable from the first position to the second position with respect to the outer cap, and the outer cap being rotatable with respect to the inner component;

a pad disposed within a chamber of the inner component, the pad impregnated with an antimicrobial element, wherein the port is receivable in the chamber as the flexible chamber engages an external surface of the port, the pad being compressed by the port to release the antimicrobial element therefrom when the inner component moves from the first position towards the second position to engage the inner component to the port, wherein the outer cap is rotatable about the inner component to a third position to disengage the inner component from the port such that the inner component remains coupled within the cavity of the outer cap upon disengagement; and wherein the inner component comprises one or more posts extending from the chamber configured to secure the pad.

18. The antimicrobial cap of claim 17 further comprising:
a housing having an open end, a closed end and defining a chamber therein, wherein the housing encloses the outer cap within the chamber; and
a lid coupled to a rim of the housing to seal the chamber from an external environment.

19. The antimicrobial cap of claim 17, wherein the attachment member of the inner component comprises at least four molded flexural attachments.

20. The antimicrobial cap of claim 17, wherein the antimicrobial element comprises alcohol, chlorhexidine gluconate, chlorhexidine-silver or mixtures thereof.

21. The antimicrobial cap of claim 17, wherein the pad comprises a foam having plurality of slots configured to couple with the flexible chamber.

22. The antimicrobial cap of claim 17, wherein the outer cap further comprises an extended open end to fully enclose the inner component to couple one or more antimicrobial caps to a packaging element.

23. An antimicrobial cap to treat a port, the antimicrobial cap comprising:

an outer cap having an open end, a closed end and defining a cavity therein, the outer cap having a sidewall with an inner surface that defines an engagement structure;

an inner component receivable in the outer cap, the inner component having a distal end comprising a first attachment member that engages with the engagement structure of the outer cap and a proximal end comprising a second attachment member to engage the port, wherein the first attachment member comprises at least four legs, wherein the second attachment member of the inner component is at least partially disposed outside the cavity of the outer cap in a first position, and the second attachment member is at least partially disposed within the cavity of the outer cap in a second position, the inner component being axially movable from the first position to the second position with respect to the outer cap, and the outer cap being rotatable with respect to the inner component; and a pad disposed within a chamber of the inner component, the pad impregnated with an antimicrobial element, wherein the port is receivable in the chamber as the second attachment member engages an external surface of the port, the pad being compressed by the port to release the antimicrobial element therefrom when the inner component moves from the first position towards the second position to engage the inner component to the port, wherein the outer cap is rotatable about the inner component to a third position to disengage the inner component from the port such that the inner component remains coupled within the cavity of the outer cap upon disengagement.

* * * * *

UNITED STATES PATENT AND TRADEMARK OFFICE
CERTIFICATE OF CORRECTION

PATENT NO. : 11,123,535 B2
APPLICATION NO. : 15/916891
DATED : September 21, 2021
INVENTOR(S) : Mark Follman et al.

It is certified that error appears in the above-identified patent and that said Letters Patent is hereby corrected as shown below:

On the Title Page

Item (12) reads:
"Foilman et al."

Should read:
-- Follman et al. --

Item (72) Inventors reads:
"Mark Foilman, Glen Rock, NJ (US); Jesse R. Dlugos, Woodbridge, CT (US); Kathryn Spencer, San Diego, CA (US); Jeffrey E. Ransden, Fairfield, CT (US); John Tanayan, Ridgefield Park, NJ (US)"

Should read:
-- Mark Follman, Glen Rock, NJ (US); Jesse R. Dlugos, Woodbridge, CT (US); Kathryn Spencer, San Diego, CA (US); Jeffrey E. Ransden, Fairfield, CT (US); John Tanayan, Ridgefield Park, NJ (US) --

Signed and Sealed this
Seventh Day of December, 2021

Drew Hirshfeld
*Performing the Functions and Duties of the
Under Secretary of Commerce for Intellectual Property and
Director of the United States Patent and Trademark Office*